United States Patent
Mehta et al.

(10) Patent No.: US 11,559,216 B1
(45) Date of Patent: Jan. 24, 2023

(54) INTEGRATED PHOTODIODE

(71) Applicant: Apple Inc., Cupertino, CA (US)

(72) Inventors: Arpit Mehta, Fremont, CA (US);
Guocheng Shao, San Jose, CA (US);
Tobias J. Harrison-Noonan, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 323 days.

(21) Appl. No.: 15/675,543

(22) Filed: Aug. 11, 2017

Related U.S. Application Data

(60) Provisional application No. 62/374,438, filed on Aug. 12, 2016.

(51) Int. Cl.
*A61B 5/024* (2006.01)
*A61B 5/00* (2006.01)

(52) U.S. Cl.
CPC .......... *A61B 5/02427* (2013.01); *A61B 5/681* (2013.01); *A61B 5/6898* (2013.01); *A61B 2560/0462* (2013.01); *A61B 2562/0238* (2013.01); *A61B 2562/046* (2013.01); *A61B 2562/146* (2013.01); *A61B 2562/182* (2013.01)

(58) Field of Classification Search
CPC ... A61B 5/02427; A61B 5/6898; A61B 5/681; A61B 2562/182; A61B 2562/146; A61B 2562/046; A61B 2560/0462; A61B 2562/0238
See application file for complete search history.

(56) References Cited

U.S. PATENT DOCUMENTS 4,739,178 A * 4/1988 Nobue ............. H01L 27/14665
257/434
5,483,261 A 1/1996 Yasutake
(Continued)

FOREIGN PATENT DOCUMENTS

JP 2000-163031 A 6/2000
JP 2002-342033 A 11/2002

OTHER PUBLICATIONS

OSI Optoelectronics (Photodiode Arrays | Standard Products | OSI Optoelectronics, An OSI Systems Company, 2010) (Year: 2010).*
(Continued)

*Primary Examiner* — Yi-Shan Yang
*Assistant Examiner* — Alexei Bykhovski
(74) *Attorney, Agent, or Firm* — Brownstein Hyatt Farber Schreck, LLP

(57) ABSTRACT

This relates to one or more integrated photodiodes on a back surface of a PPG device. The one or more integrated photodiodes can reduce the gap between one or more windows and the active area of the photodiode(s) to increase the PPG signal strength without affecting the depth of light penetration into skin tissue. In some examples, the photodiode stackup can contact the surface of the windows. In some examples, the photodiode stackups can exclude a separate substrate. In some examples, the photodiode stackup can be deposited on the inner surface of the windows opposite the outer surface of the device. In some examples, the photodiode stackup can be deposited on the back surface and/or outer surface of the device. In this manner, PPG sensors can be included in the device without the need for extra layers and measurement accuracy can be improved due to lower light loss.

17 Claims, 21 Drawing Sheets

(56) References Cited

U.S. PATENT DOCUMENTS

| | | | |
|---|---|---|---|
| 5,488,204 A | 1/1996 | Mead et al. | |
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,663,607 B2 | 2/2010 | Hotelling et al. | |
| 8,479,122 B2 | 7/2013 | Hotelling et al. | |
| 9,392,946 B1 * | 7/2016 | Sarantos | A61B 5/14552 |
| 2006/0197753 A1 | 9/2006 | Hotelling | |
| 2010/0041161 A1 * | 2/2010 | Ferrao De Paiva Martins | G01N 33/54373 436/86 |
| 2013/0289381 A1 * | 10/2013 | Oraevsky | A61B 5/7425 600/407 |
| 2014/0084405 A1 * | 3/2014 | Tsuchiya | H01L 27/14627 257/432 |
| 2014/0231635 A1 * | 8/2014 | Kerness | G01S 17/026 250/226 |
| 2015/0032009 A1 * | 1/2015 | LeBoeuf | A61B 5/00 600/476 |
| 2016/0058309 A1 | 3/2016 | Han | |
| 2016/0058312 A1 | 3/2016 | Han et al. | |
| 2016/0061726 A1 | 3/2016 | Ness et al. | |
| 2016/0081552 A1 * | 3/2016 | Wojtczuk | A61B 5/0059 600/473 |
| 2017/0332923 A1 * | 11/2017 | Masuda | A61B 5/7214 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

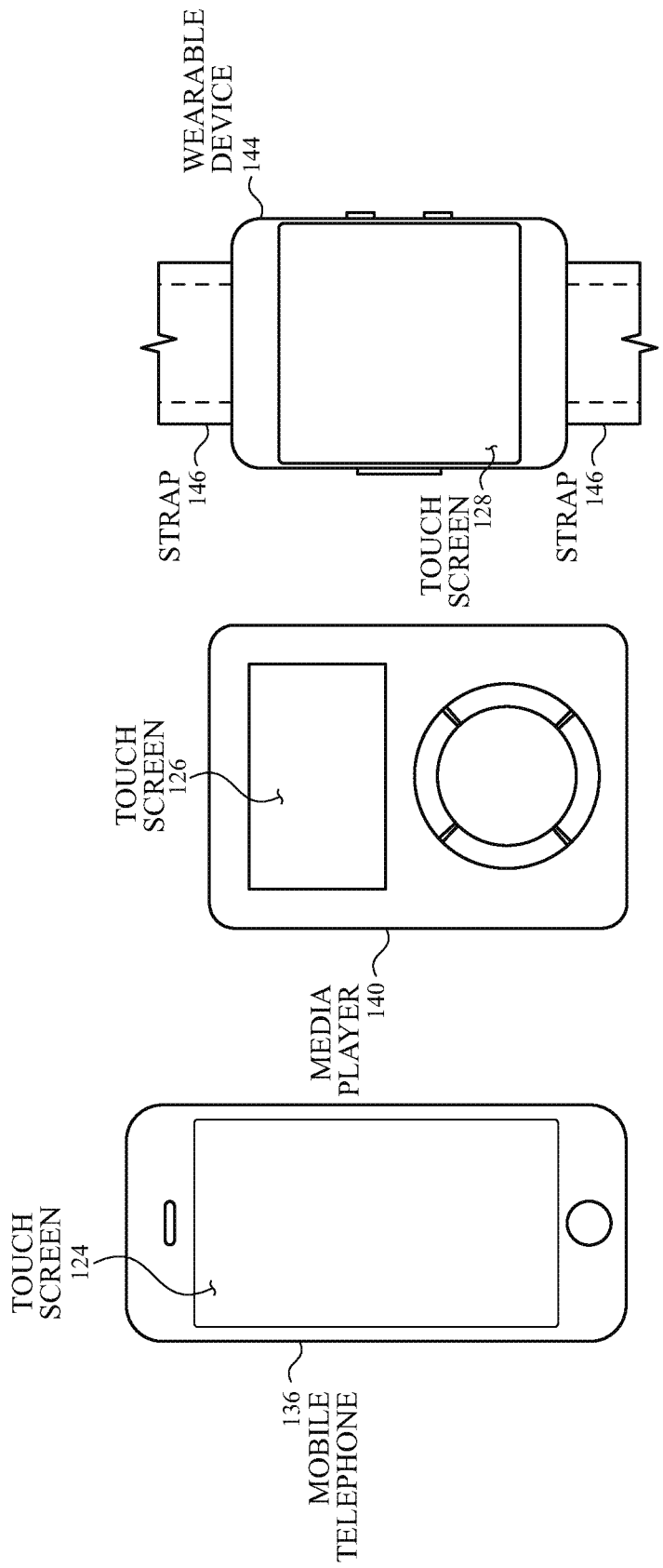

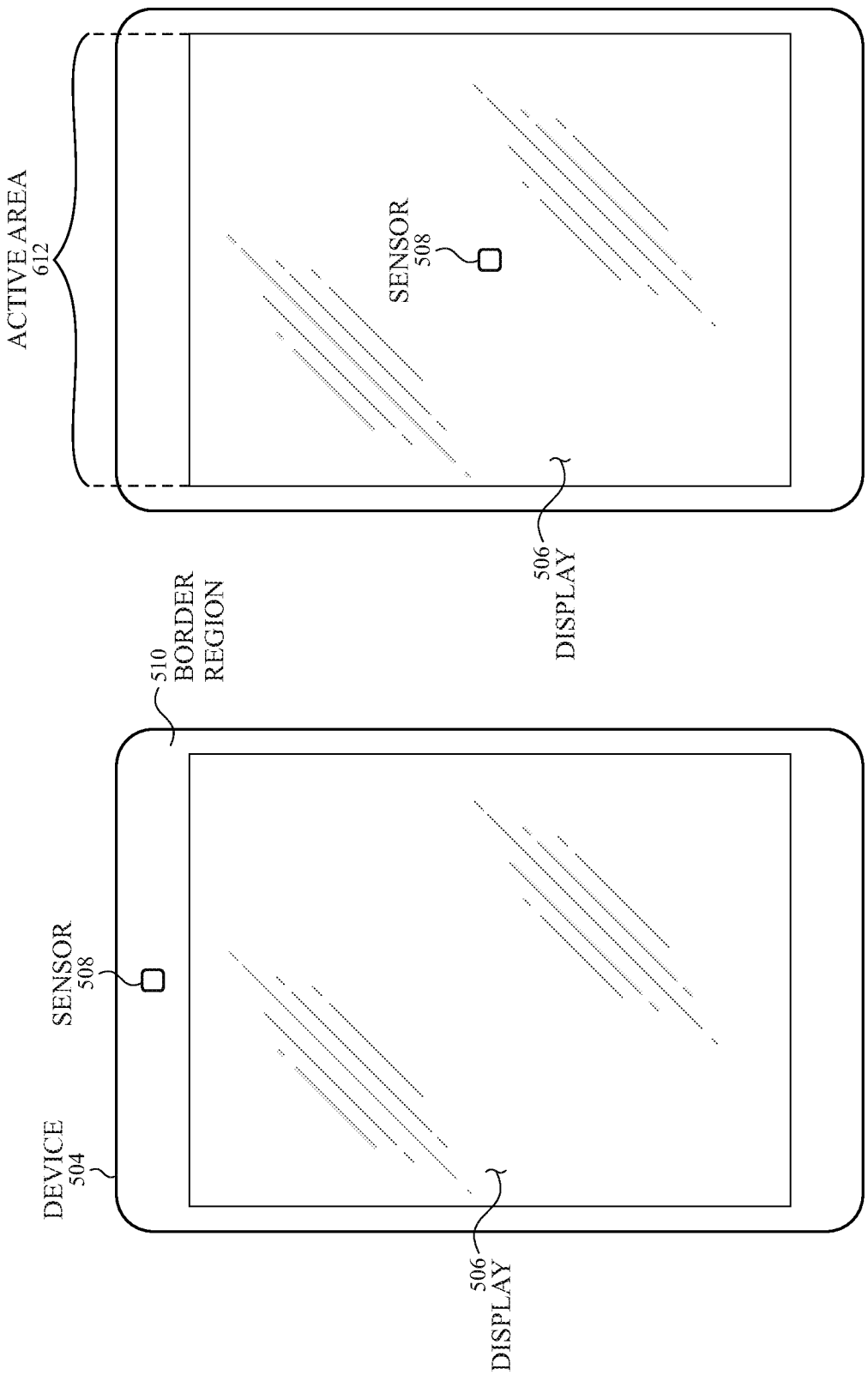

INTEGRATED PHOTODIODE

CROSS REFERENCE TO RELATED APPLICATIONS

This application claims the benefit under 35 U.S.C. § 119(e) of U.S. Patent Application No. 62/374,438 filed Aug. 12, 2016, the contents of which are incorporated herein by reference in their entirety for all purposes.

FIELD

This relates generally to a device that measures optical signal(s), and, more particularly, to one or more integrated photodiodes on a back surface of the device.

BACKGROUND

A device can include one or more photodiodes located on a back surface of the device, where the photodiodes can be configured for measuring one or more optical properties. For example, the photodiodes can be used to measure ambient light and/or determine whether the user's wrist is located in close proximity to the device. Another exemplary use for photodiodes can include photoplethysmographic (PPG) sensing. PPG sensing can include measuring optical signals to derive corresponding physiological signals (e.g., a pulse rate). In a basic form, PPG systems can employ a light source or light emitter that injects light into the user's tissue, and a light sensor to receive light that can reflect and/or scatter and can exit the tissue. The received light can include light with an amplitude that is modulated as a result of pulsatile blood flow (i.e., "signal") and parasitic, non-signal light with an amplitude that can be modulated (i.e., "noise" or "artifacts") and/or unmodulated (i.e., DC). However, in some examples, the path length of reflected and/or scattered light received by the light sensor may be long, which can result in a low signal strength and difficulty in accurately determining the user's pulse rate.

One way to increase the signal intensity or signal strength can be to decrease the distance between the light sensor and light emitter. Although the lateral separation between the light sensor and light emitter can be reduced, such change in lateral separation can affect the depth that the light can penetrate into the skin. An alternative way to increase the signal strength without affecting the depth of light penetration may be needed.

SUMMARY

This relates to one or more integrated photodiodes on a back surface (e.g., underside) of a PPG device. The one or more integrated photodiodes can reduce the gap between one or more windows and the active area of the photodiode(s) (i.e., light sensor(s)) to increase the PPG signal strength without affecting the depth of light penetration into skin tissue. In some examples, the photodiode stackup can contact the surface of the windows. In some examples, the photodiode stackups can exclude a separate substrate. In this manner, PPG sensors can be included in the device without the need for extra layers (e.g., a separate substrate), which can result in improved measurement accuracy and reduced power consumption due to lower light loss.

BRIEF DESCRIPTION OF THE DRAWINGS

FIGS. 1A-1C illustrate systems in which examples of the disclosure can be implemented.

FIG. 5A illustrates a top view of an exemplary device including a sensor according to examples of the disclosure.

FIG. 5B illustrates a top view of an exemplary device including a sensor according to examples of the disclosure.

DETAILED DESCRIPTION

Figure 2A:
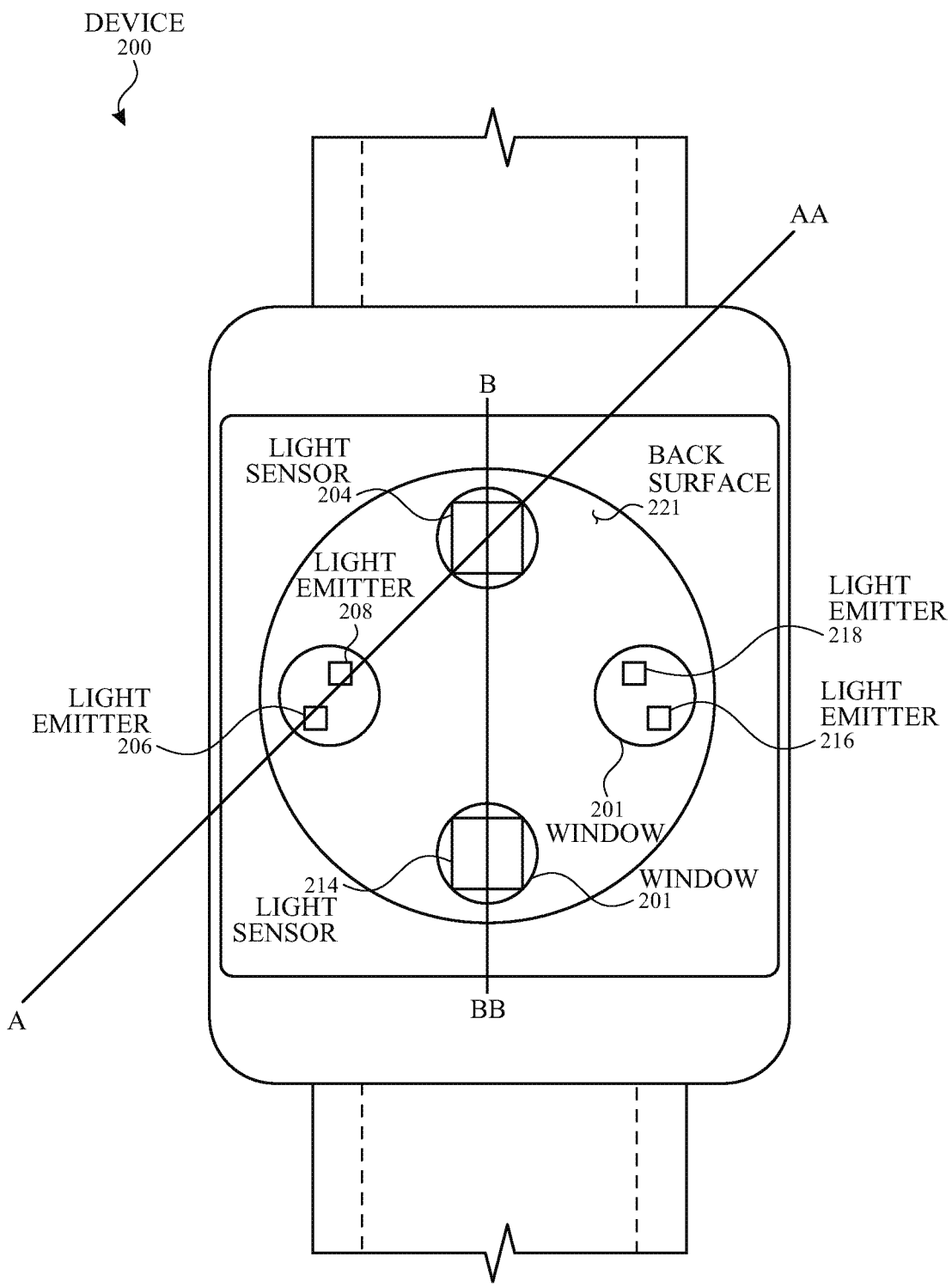
FIG. 2A illustrates a top view of an exemplary electronic device including dedicated photodiodes for PPG measurements according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details.

Representative applications of methods and apparatus according to examples of the present disclosure are described in this section. These examples are being provided solely to add context and aid in the understanding of the described examples. It will thus be apparent to one skilled in the art that the described examples may be practiced without some or all of the specific details. In other instances, well-known process steps have been described in detail in order to avoid unnecessarily obscuring the described examples. Other applications are possible, such that the following examples should not be taken as limiting.

A device can include one or more photodiodes located on a back surface of the device, where the photodiodes can be configured for measuring one or more optical properties. For example, the photodiodes can be used to measure ambient light and/or determine whether the user's wrist is located in close proximity to the device. Conventionally, the photodiodes are formed and located on a substrate separate from a surface (e.g., a back surface included in the external housing) of the device. In some instances, integrating the photodiode(s) can allow the photodiode to be located closer to objects (e.g., the user's wrist) of interest and can decrease fabrication complexity, for example.

A photoplethysmographic (PPG) signal can be measured by PPG systems to derive corresponding physiological signals (e.g., pulse rate). Such PPG systems can be designed to be sensitive to changes in blood in a user's tissue that can result from fluctuations in the amount or volume of blood or blood oxygen in the vasculature of the user. In a basic form, PPG systems can employ a light emitter (or light source) that injects light into the user's tissue, and a light sensor (or light detector) that can receive light that reflects and/or scatters and exits the tissue. The PPG signal is the amplitude of reflected and/or scattered light that can be modulated with volumetric change in blood volume in the tissue. In some examples, the path length of reflected and/or scatter light received by the light sensor may be long, which can result in a low signal strength and difficulty in accurately determining the user's pulse rate. One way to increase the signal intensity or signal strength can be to decrease the distance between the light sensor and light emitter. Although the lateral separation between the light sensor and light emitter can be reduced, such change in lateral separation can affect the depth that the light can penetrate into the skin. An alternative way to increase the signal strength without affecting the depth of light penetration may be needed.

This disclosure relates to one or more integrated photodiodes on a back surface of a PPG device. The one or more integrated photodiodes can reduce the gap between one or more windows and the active area of the photodiode(s) (i.e., light sensor(s)) to increase the PPG signal strength without affecting the depth of light penetration into skin tissue. In some examples, the photodiode stackup can contact the surface of the windows. In some examples, the photodiode stackups can exclude a separate substrate. In this manner, PPG sensors can be included in the device without the need for extra layers (e.g., a separate substrate), and measurement accuracy can be improved due to lower light loss. Although the disclosure discusses integrated photodiodes in the context of a PPG device and PPG measurements, examples of the disclosure are not so limited and can be applied to other types of devices and applications associated with optical sensing.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the integrated photodiodes as disclosed.

Figure 2B:
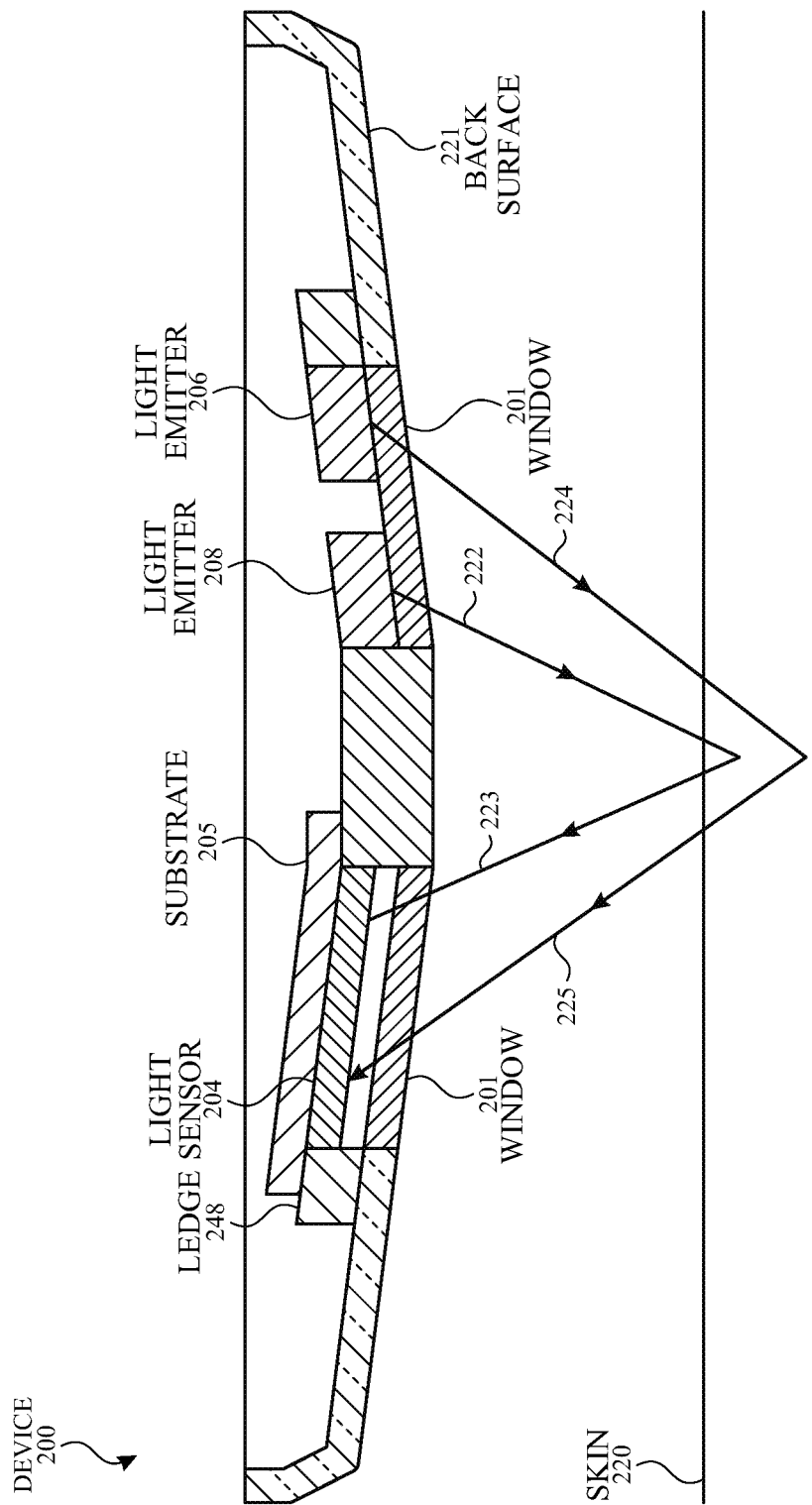
FIG. 2B illustrates a cross-sectional view of an exemplary electronic device including dedicated photodiodes for PPG measurements according to examples of the disclosure.

FIG. 2A illustrates a top view and FIG. 2B illustrates a cross-sectional view (along the line A-AA indicated in FIG. 2A) of an exemplary electronic device including dedicated photodiodes for PPG measurements according to examples of the disclosure. Device 200 can include light emitter 206, light emitter 208, light emitter 216, and light emitter 218 located on a surface of device 200. Device 200 can further include light sensor 204 and light sensor 214 located on the surface of device 200. Light emitter 206, light emitter 208, light emitter 216, light emitter 218, light sensor 204, and light sensor 214 can be configured with each active area facing towards skin 220 of a user. Light emitter 206, light emitter 208, light emitter 216, and light emitter 218 can be any type of light source, including but not limited to, light emitting diodes (LEDs), incandescent lights, fluorescent lights, organic light emitting diodes (OLEDs), and electroluminescent diodes (ELDs). Light sensor 204 and light sensor 214 can be any type of optical sensing device such as a photodiode. In some examples, light emitter 206 and light emitter 216 can be the same type of light emitter. In some examples, light emitter 208 and light emitter 218 can be the same type of light emitter. In some examples, light emitter 206 and light emitter 216 can be configured to emit a first wavelength, and light emitter 208 and light emitter 218 can be configured to emit a second wavelength, different from the first wavelength. In some examples, light sensor 204 and light sensor 214 can be symmetrically placed (i.e., located the same distance away) with respect to the center of back surface 221.

Windows 201 can be located between the optical components (e.g., light sensor 204 and light sensor 214) and skin 220 (and/or the surface of device 200). Light emitter 208 can emit light 222. A portion of light 222 can be absorbed by one or more vasculature structures located in skin 220, and a portion of light 222 can reflect back as light 223. Light sensor 204 can detect light 223 and can generate a signal indicative of one or more properties of light 223. Light emitter 206 can emit light 224. A portion of light 224 can be absorbed by one or more vasculature structures located in skin 220, and a portion of light 224 can reflect back as light 225. Light sensor 204 can detect light 225 and can generate a signal indicative of one or more properties of light 225. A processor or controller can receive the signals generated by light sensor 204 and can utilize the information included in the signals to determine the user's physiological signals.

Figure 2C:
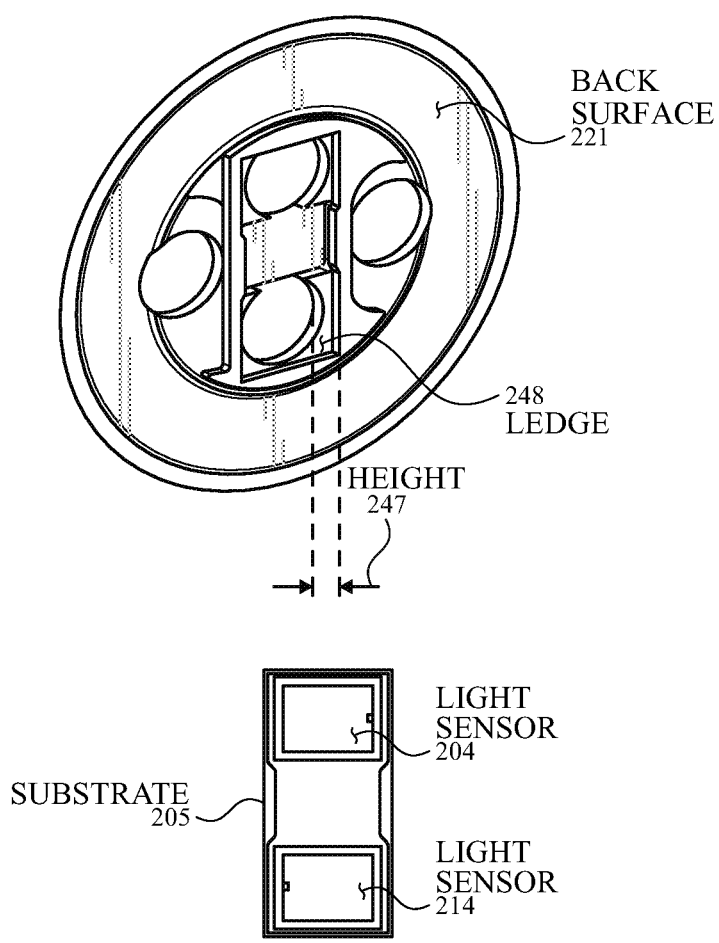
FIG. 2C illustrates a partial bottom view of an exemplary electronic device including dedicated photodiodes for PPG measurements according to examples of the disclosure.
Figure 2D:
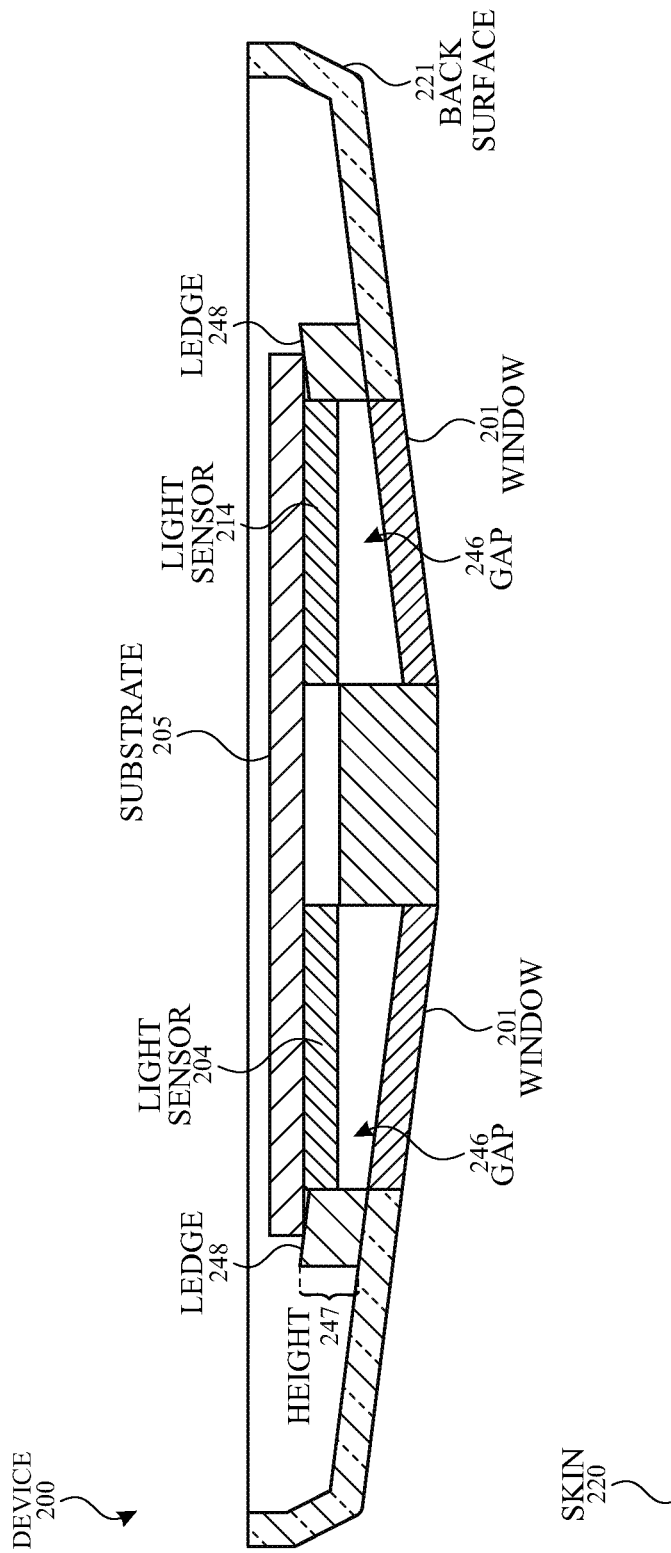
FIG. 2D illustrates a cross-sectional view of an exemplary electronic device including dedicated photodiodes for PPG measurements according to examples of the disclosure.

FIG. 2C illustrates a partial bottom view and FIG. 2D illustrates a cross-sectional view (along the line B-BB indicated in FIG. 2A) of an exemplary electronic device including dedicated photodiodes for PPG measurements according to examples of the disclosure. Back surface 221 can include ledge 248. Ledge 248 can be any type of physical structure configured to provide mechanical support to one or more optical components. Light sensor 204 and light sensor 214 can be mounted or formed on the same substrate 205. In some examples, light sensor 204 and light sensor 214 can include discrete optical components. FIG. 2C shows the active areas of light sensor 204 and light sensor 214. When device 200 is assembled, the active areas of light sensor 204 and light sensor 214 can be facing windows 201, as illustrated in FIG. 2D.

Ledge 248 can have a height 247, which can cause light sensor 204 and light sensor 214 to be seated a fixed distance away from windows 201 or from the surface of back surface 221. As a result, gap 246 can exist between window 201 and the active area of light sensor 204. Additionally, gap 246 can exist between window 201 and the active area of light sensor 214. In some examples, gap 246 can be 0.8 mm. In some examples, gap 246 can be 1 mm. Gap 246 can cause loss of reflected light, preventing the reflected light from reaching the active area of light sensor 204 and light sensor 214. The loss of reflected light can result in decreased photodiode efficiency, which can lead to degradation in the generated signals. Degradation in the generated signals can require the system to increase the power of light emitted by the light emitters (e.g., light emitter 206, light emitter 208, light emitter 216, and light emitter 218) and/or can result in poor measurement accuracy.

Figure 2E:
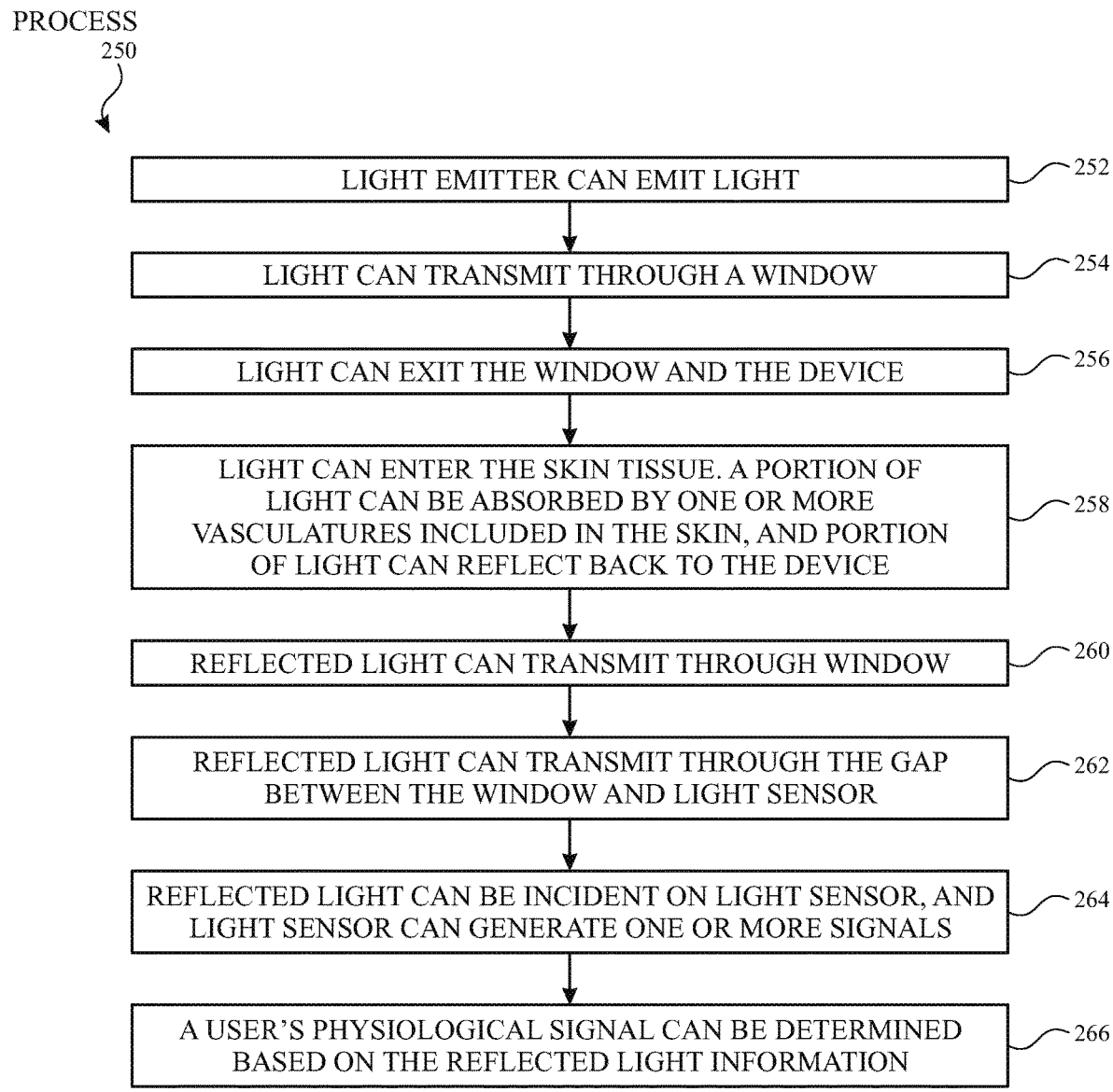
FIG. 2E illustrates an exemplary method for operating an electronic device including dedicated photodiodes for PPG measurements according to examples of the disclosure.

FIG. 2E illustrates an exemplary method for operating an electronic device including dedicated photodiodes for PPG measurements according to examples of the disclosure. In step 252 of process 250, light emitter (e.g., light emitter 208) can emit light (e.g., light 222) towards the user (e.g., skin 220). In step 254 of process 250, light can pass through a window (e.g., window 201). In step 256 of process 250, light can exit the window (e.g., window 201) and the device (e.g., device 200). In step 258 of process 250, light (e.g., light 222) can enter the skin tissue (e.g., skin 220). A portion of light can be absorbed by one or more vasculatures included in the skin, and a portion of light (e.g., light 223) can reflect back to the device (e.g., device 200). In step 260 of process 250, the reflected light (e.g., light 223) can enter the device and can pass through the window (e.g., window 201). In step 262 of process 250, the reflected light (e.g., light 223) can pass through the gap (e.g., gap 246) between the window (e.g., window 201) and light sensor (e.g., light sensor 204). In step 264 of process 250, the reflected light (e.g., light 223) can be incident on the active area of light sensor (e.g., light sensor 204), and the light sensor can generate one or more signals including reflected light information. In step 266 of process 250, the user's physiological signal can be determined based on the reflected and/or back-scattered light information.

Figure 2F:
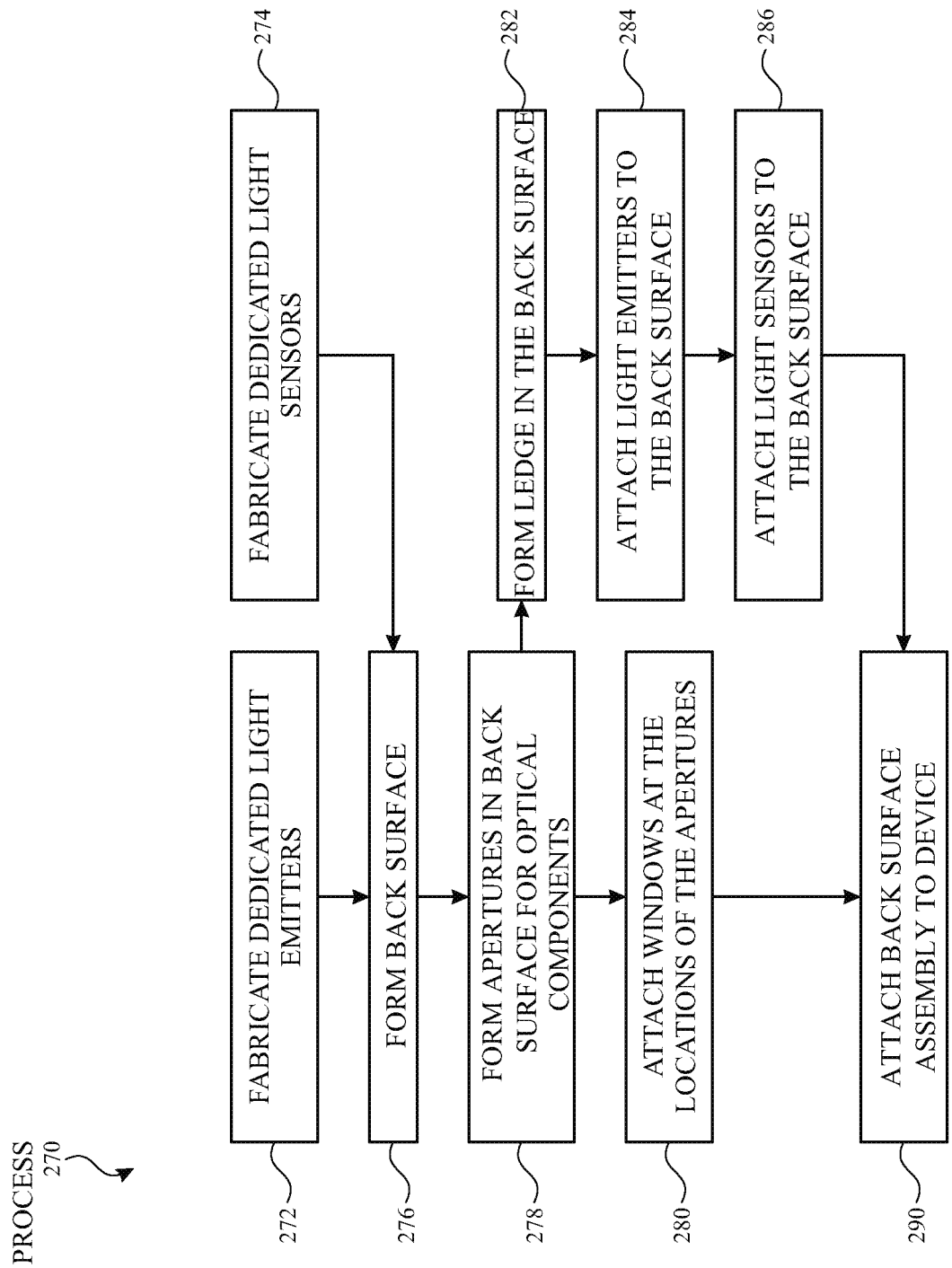
FIG. 2F illustrates an exemplary method for fabricating an electronic device including dedicated photodiodes for PPG measurements according to examples of the disclosure.

FIG. 2F illustrates an exemplary method for fabricating an electronic device including dedicated photodiodes for PPG measurements according to examples of the disclosure. In step 272 of process 270, dedicated (i.e., separately fabricated, packaged, and/or diced) light emitters (e.g., light emitter 206 and light emitter 208) can be fabricated. In step 274 of process 270, dedicated light sensors (e.g., light sensor 204 and light sensor 214) can be fabricated. In step 276 of process 270, the back surface (e.g., back surface 221) can be formed. In step 278 of process 270, apertures can be formed in the back surface for the optical components. In step 280 of process 270, windows (e.g., window 201) can be attached at the location(s) of the apertures. In step 282 of process 270, one or more ledges (e.g., ledge 248) can be formed in the back surface (e.g., back surface 221). In step 284 of process 270, one or more light emitters (e.g., light emitter 206 and light emitter 208) can be attached to the back surface (e.g., back surface 221). In step 286 of process 270, one or more light sensors (e.g., light sensor 204 and light sensor 214) can be attached to the back surface (e.g., back surface 221). In some examples, a plurality of wires can be attached to the light emitters and light sensors. In step 290 of process 270, the back surface assembly (i.e., back surface and attached light emitters, light sensors, and windows) can be attached to the device (e.g., device 200).

One way to increase the signal intensity or signal strength can be to decrease the separation distance between a light sensor and a light emitter. Although the lateral separation between the light sensor and light emitter can be reduced, such change in lateral separation can affect the depth that the light can penetrate into the skin. An alternative way to increase the signal strength without affecting the depth of light penetration may be needed.

Figure 3A:
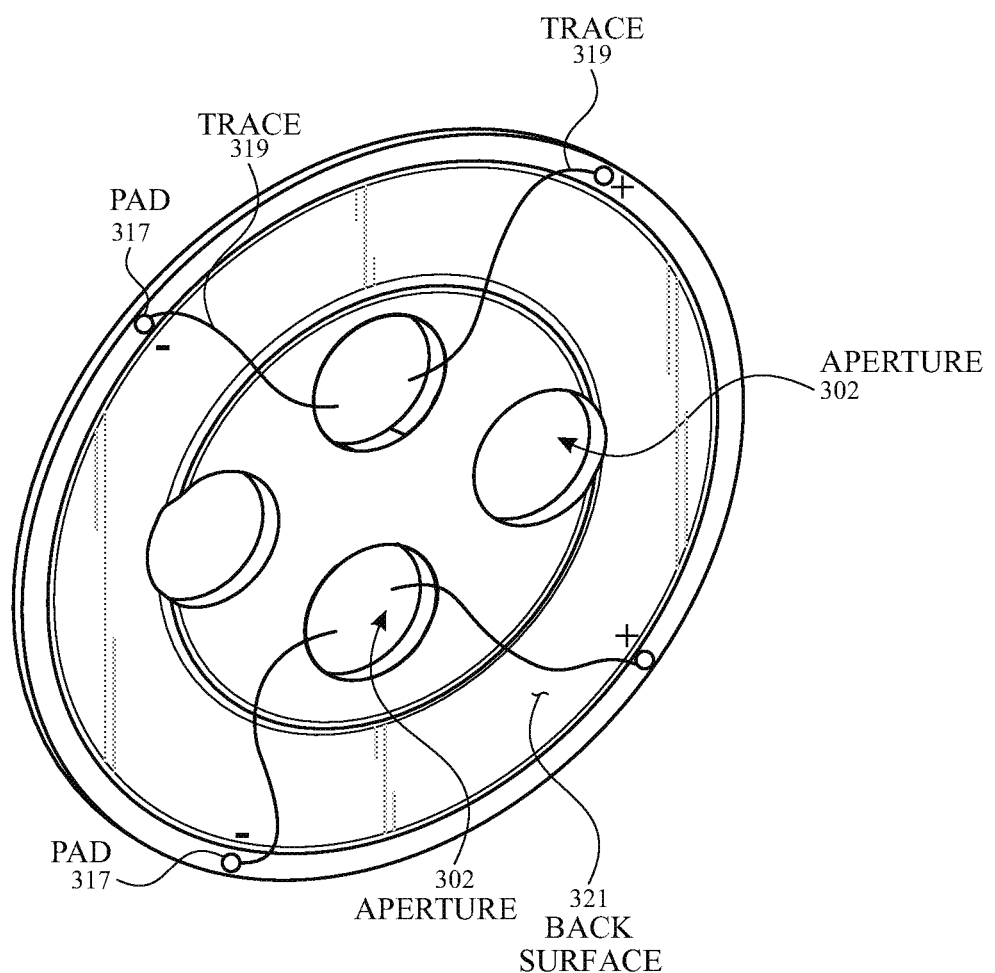
FIG. 3A illustrates a partial bottom view of an exemplary electronic device including integrated photodiodes for PPG measurements according to examples of the disclosure.
Figure 3B:
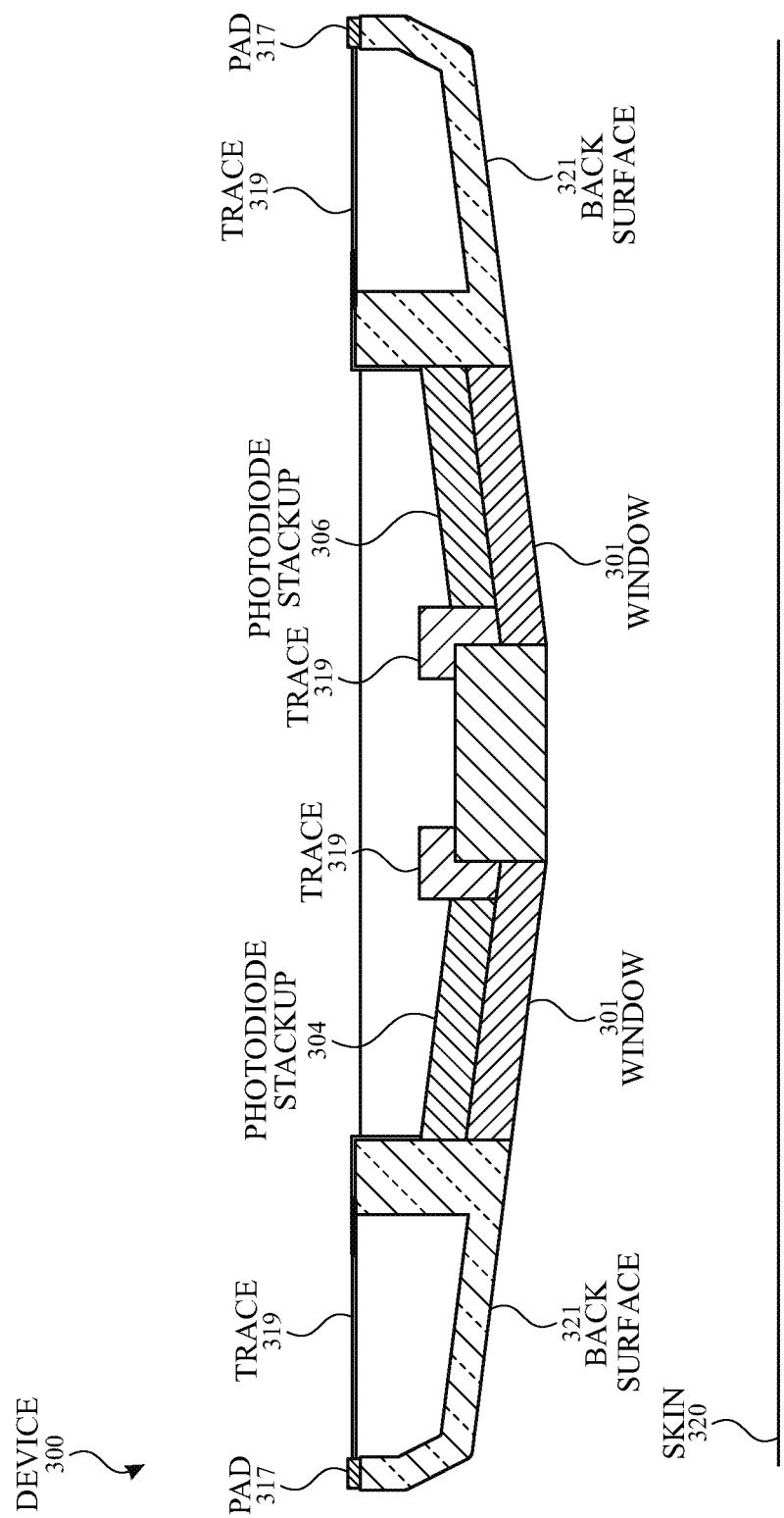
FIG. 3B illustrates a cross-sectional view of an exemplary electronic device including integrated photodiodes for PPG measurements according to examples of the disclosure.

FIG. 3A illustrates a partial bottom view and FIG. 3B illustrates a cross-sectional view of an exemplary electronic device including integrated photodiodes for PPG measurements according to examples of the disclosure. Device 300 can include a plurality of apertures 302. Apertures 302 can be configured to allow light to pass through. In some examples, windows 301 can be located in close proximity to apertures 302. Device 300 can further include back surface 321.

To reduce the gap between the windows and the active area of the light sensors, photodiode stackup 304 can be deposited on window 301 and photodiode stackup 306 can be deposited on window 301. In some examples, photodiode stackup 306 can contact the surface of window 301 and can be integrated into back surface 321. That is, the photodiodes may not be separately packaged and/or fabricated. Photodiode stackup 304 and photodiode stackup 306 can include one or more layers that form the photodiode such as the P and N layers in a PN photodiode. In some examples, photodiode stackup 304 and photodiode stackup 306 can be formed without a separate substrate (i.e., a base layer upon which a material is deposited onto). In some examples, photodiode stackup 304 and photodiode stackup 306 can be deposited on the same window. In some examples, photodiode stackup 304 and photodiode stackup 306 can be deposited on different windows. In some examples, one or more layers, excluding air, can be included in the photodiode stackup and can be located between window 301 and a photodiode stackup. In some examples, the one or more layers can contact window 301 (i.e., reflected light can pass through a layer-window interface). The one or more layers can include, but are not limited to, silicon dioxide and titanium dioxide. In this manner, PPG sensors can be included in device 300 without the need for extra layers (e.g., a separate substrate), and measurement accuracy can be improved due to lower light loss.

Plurality of traces 319 can contact photodiode stackup 304 and can be configured for routing signals to and from the photodiode stackup 304 to plurality of pads 317. Additionally, plurality of traces 319 can contact photodiode stackup 306 and can be configured for routing signals to and from the photodiode stackup 306 to plurality of pads 317. Plurality of pads 317 can be configured to allow one or more electrical connectors to transmit and/or receive signals to/from a photodiode stackup. In some examples, plurality of traces 319 and/or plurality of pads 317 can be printed/deposited on back surface 321. In some examples, plurality of traces 319 and/or plurality of pads 317 can contact back surface 321. In some examples, plurality of traces 319 and/or plurality of pads 317 can be deposited on the side of back surface 321 opposite skin 320 and/or window 301. In some examples, at least a portion of plurality of traces 319 can be sputtered on the sidewall of back surface 321. In some examples, plurality of traces 319 and/or plurality of pads 317 can include conductive ink. In some examples, device 300 can include a conductive glue to connect plurality of traces 319 to a photodiode stackup.

In some examples, windows 301 can be configured to provide mechanical support to photodiode stackup 304 and photodiode stackup 306. Windows 301 can also be transparent and can be configured to allow light to pass through. In some examples, windows 301 can include sapphire. In some examples, windows 301 can further be configured to protect photodiode stackup 304 and photodiode stackup 306 from unwanted environmental conditions (e.g., dust, external forces or pressure, moisture, etc.) In some examples, windows 301 can include Fresnel lenses.

In some examples, one or more of photodiode stackup 304 and photodiode stackup 306 can be configured to obscure the optical components from the human eye. In some examples, photodiode stackup 304 and/or photodiode 306 can be formed by sputtering black photodiodes.

In some examples, windows 301 can include zirconia. The zirconia windows can be configured to be transparent or semi-transparent by adjusting the thickness of the window, for example (e.g., the zirconia window can be made thinner for better transparency). The zirconia material can obscure the optical components from the human eye while also allowing light to pass through to the photodiode stackup(s).

Figure 3C:
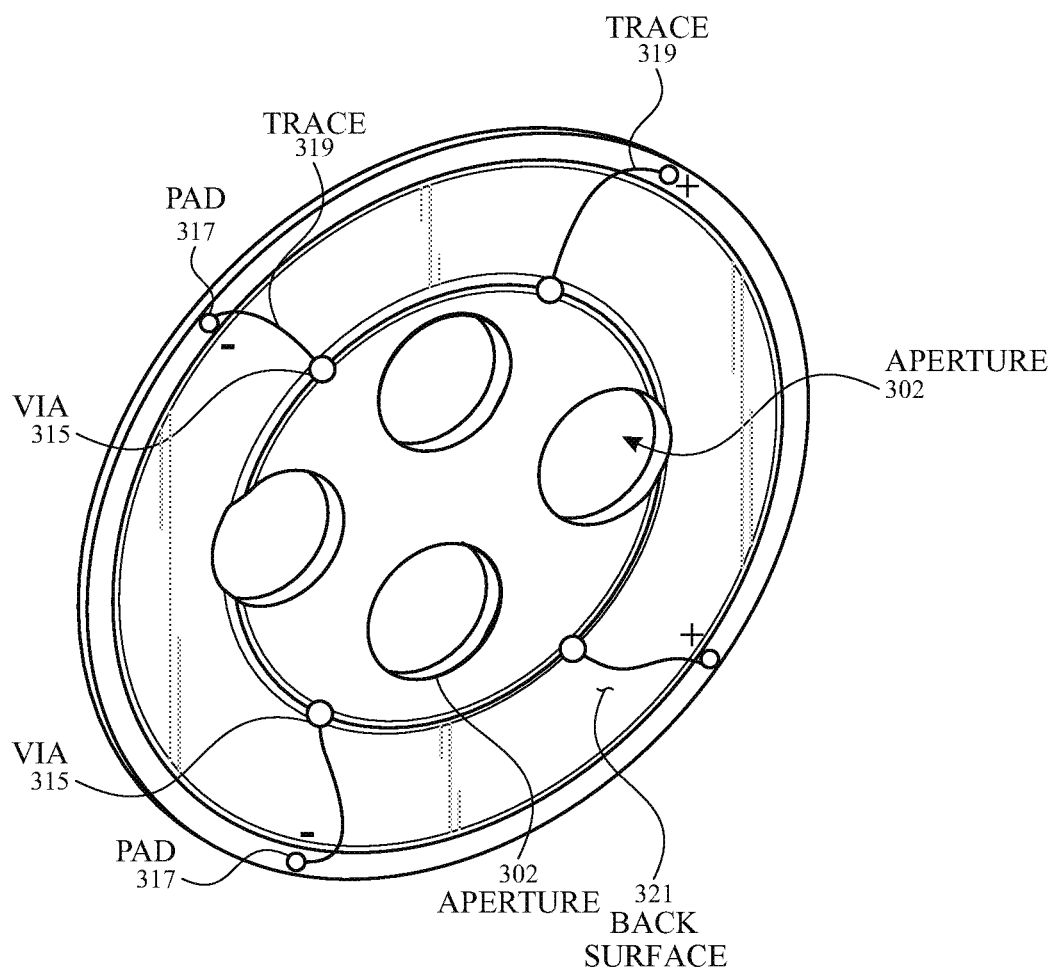
FIG. 3C illustrates a partial bottom view of an exemplary electronic device including integrated photodiodes for PPG measurements according to examples of the disclosure.

FIG. 3C illustrates a partial bottom view of an exemplary electronic device including integrated photodiodes for PPG measurements according to examples of the disclosure. In some examples, signals to and from photodiode stackups can be routed by way of plurality of traces 319 and/or plurality of vias 315. In some examples, plurality of vias 315 can be configured to allow photodiode stackups to be routed on one side of back surface 321. In some examples, plurality of pads 317 can be located on another side of back surface 321 (not shown).

Figure 3D:
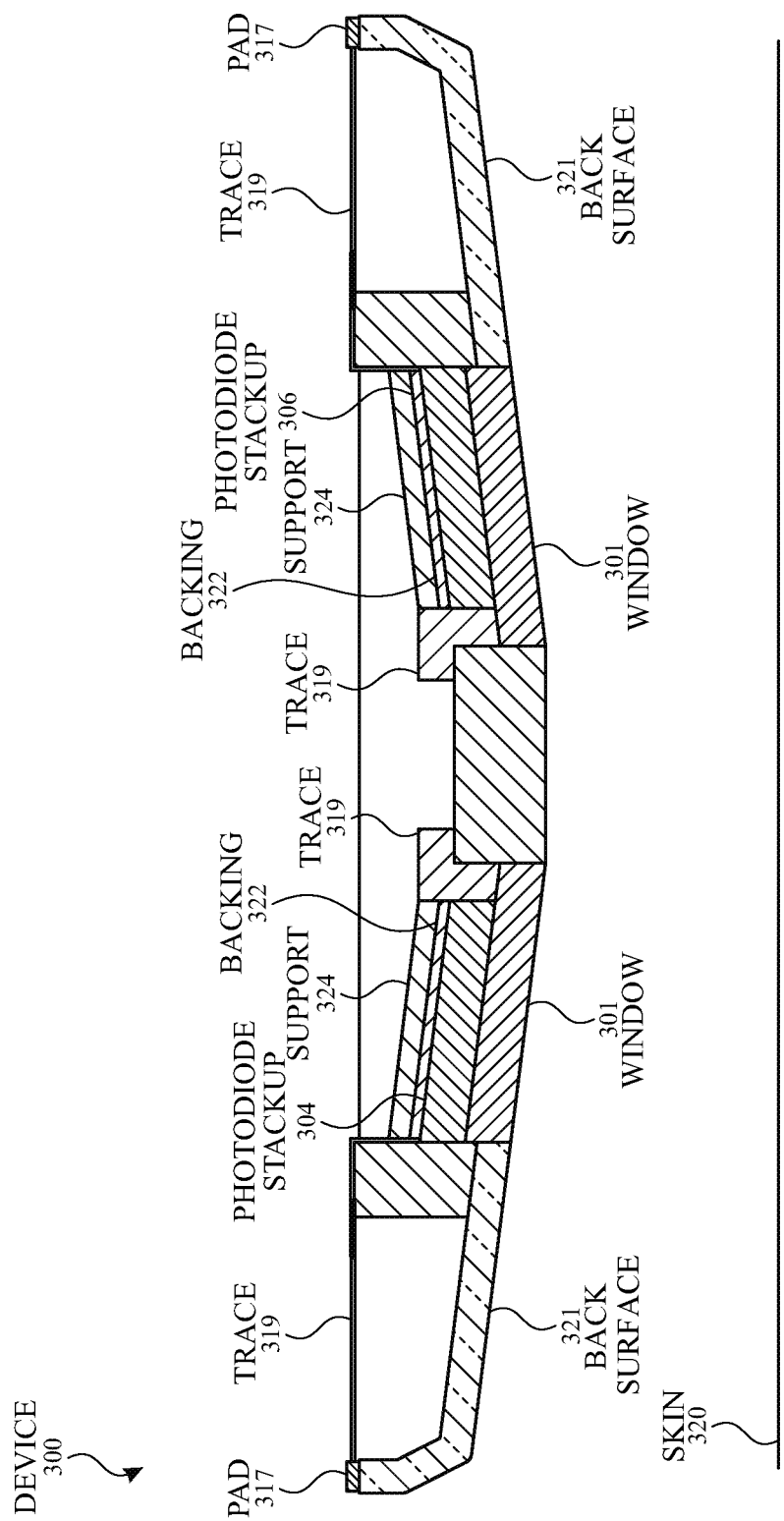
FIG. 3D illustrates a cross-sectional view of an exemplary electronic device including support and backing according to examples of the disclosure.

The electronic device can include one or more additional layers for cosmetic purposes, support purposes, or both. FIG. 3D illustrates a cross-sectional view of an exemplary electronic device including support and backing according to examples of the disclosure. Device 300 can include a backing 322 disposed on photodiode stackup 340 and photodiode stackup 306. Backing 322 can be included for aesthetic purposes. In some examples, backing 322 can include one or more layers of black ink. In some examples, the thickness of the photodiode can be increased for aesthetic purposes. Support 324 can be disposed on backing 322. Support 324 can be configured for providing support and/or protection to photodiode stackup 304, photodiode stackup 306, and/or backing 322. In some examples, support 324 can include an epoxy. In some examples, support 324 can include a dielectric coating. In some examples, backing 322 can be configured for providing support and/or protection. In some examples, a protective layer (e.g., a neutral layer) can be inserted between backing 322 and support 324.

Figure 3E:
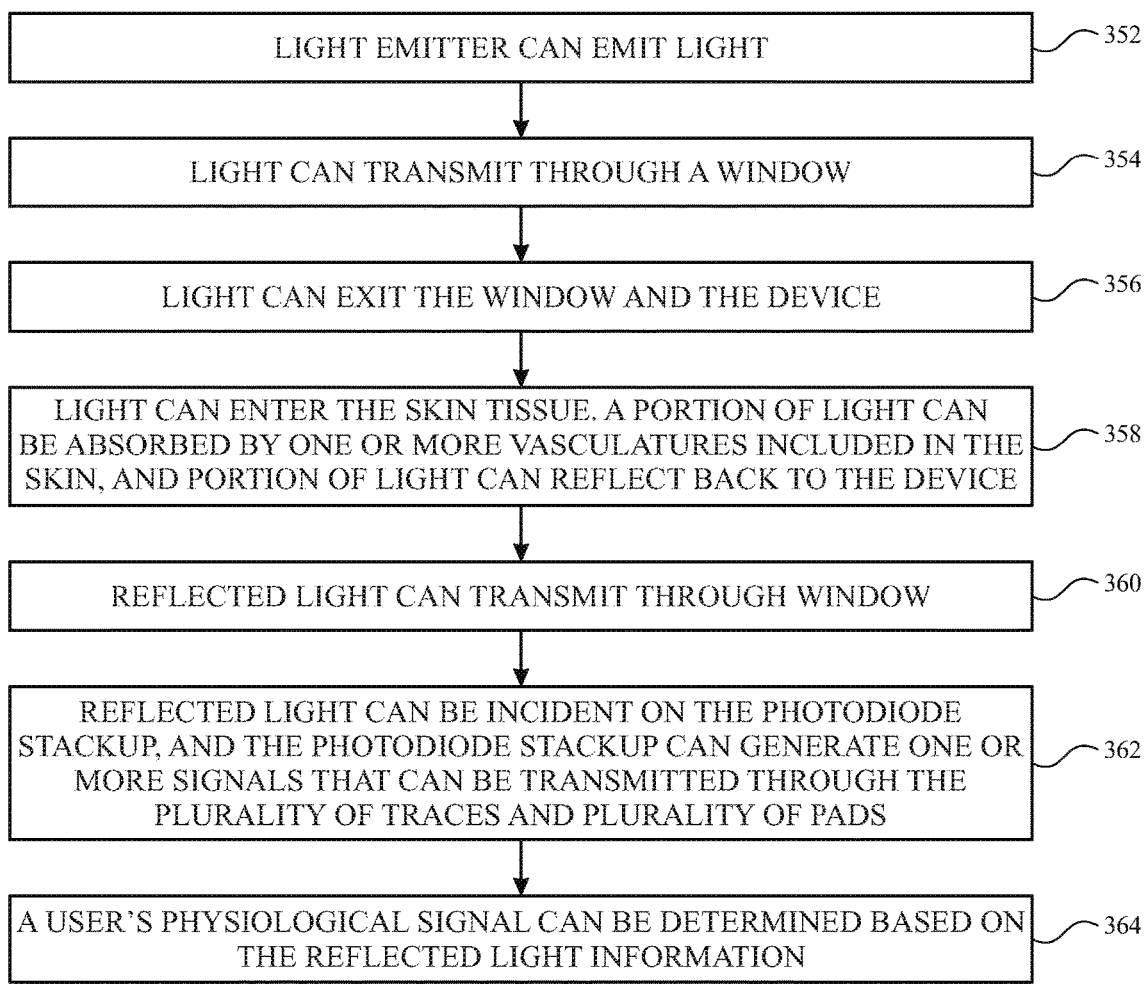
FIG. 3E illustrates an exemplary method for operating an electronic device including integrated photodiodes according to examples of the disclosure.

FIG. 3E illustrates an exemplary method for operating an electronic device including integrated photodiodes according to examples of the disclosure. In step 352 of process 350, light emitter (e.g., light emitter 308) can emit light towards the user (e.g., skin 320). In step 354 of process 350, light can pass through a window (e.g., window 301). In step 356 of process 350, light can exit the window (e.g., window 301) and the device (e.g., device 300). In step 358 of process 350, light can enter the skin tissue (e.g., skin 320). A portion of light can be absorbed by one or more vasculatures included in the skin, and a portion of light can reflect back to the device (e.g., device 300). In step 360 of process 350, the reflected light can pass through the window (e.g., window 301). In step 362 of process 350, the reflected light can be incident on the photodiode stack (e.g., photodiode stackup 304 and photodiode stackup 306) and/or one or more layers, excluding air, located between a window and the photodiode stackup. In some examples, reflected light exiting the window may not have to pass through air. The photodiode stackup can generate one or more signals that can be transmitted to a processor or controller using the plurality of traces (e.g., plurality of traces 319) and the plurality of pads (e.g., plurality of pads 317). In step 364 of process 350, the user's physiological signal can be determined based on the reflected and/or back-scattered light information.

Figure 3F:
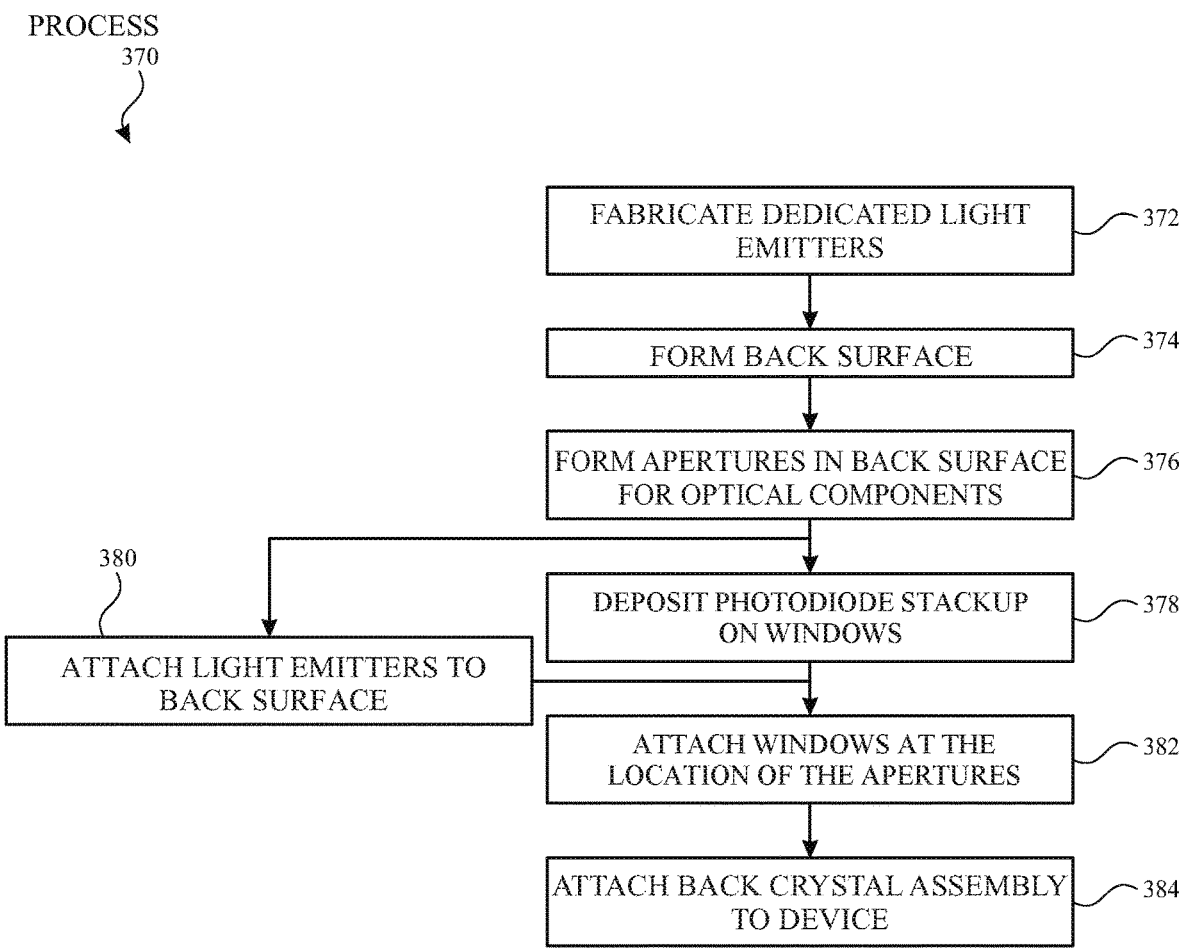
FIG. 3F illustrates an exemplary method for fabricating an exemplary electronic device including integrated photodiodes according to examples of the disclosure.

FIG. 3F illustrates an exemplary method for fabricating an exemplary electronic device including integrated photodiodes according to examples of the disclosure. In step 372 of process 370, dedicated light emitters can be fabricated. In step 374 of process 370, the back surface (e.g., back surface 321) can be formed. In step 376 of process 370, apertures (e.g., apertures 302) can be formed in the back surface for the optical components (e.g., light emitters and light sensors). In step 378 of process 370, each photodiode stackup (e.g., photodiode stackup 304 and photodiode stackup 306) can be deposited on the windows (e.g., window 301). In step 380 of process 370, the light emitters can be attached to the back surface (e.g., back surface 321). In step 382 of process 370, the windows (e.g., window 301) can be attached at the location of the apertures. In some examples, the photodiode stackup can be deposited on the windows after attaching the windows at the location of the apertures. In step 384 of process 370, the back surface assembly (i.e., back surface, attached light emitters and windows, and deposited light sensors) can be attached to the device (e.g., device 300). In some examples, the photodiode stackup can be deposited on the windows prior to the windows being attached to the back surface.

Figure 4A:
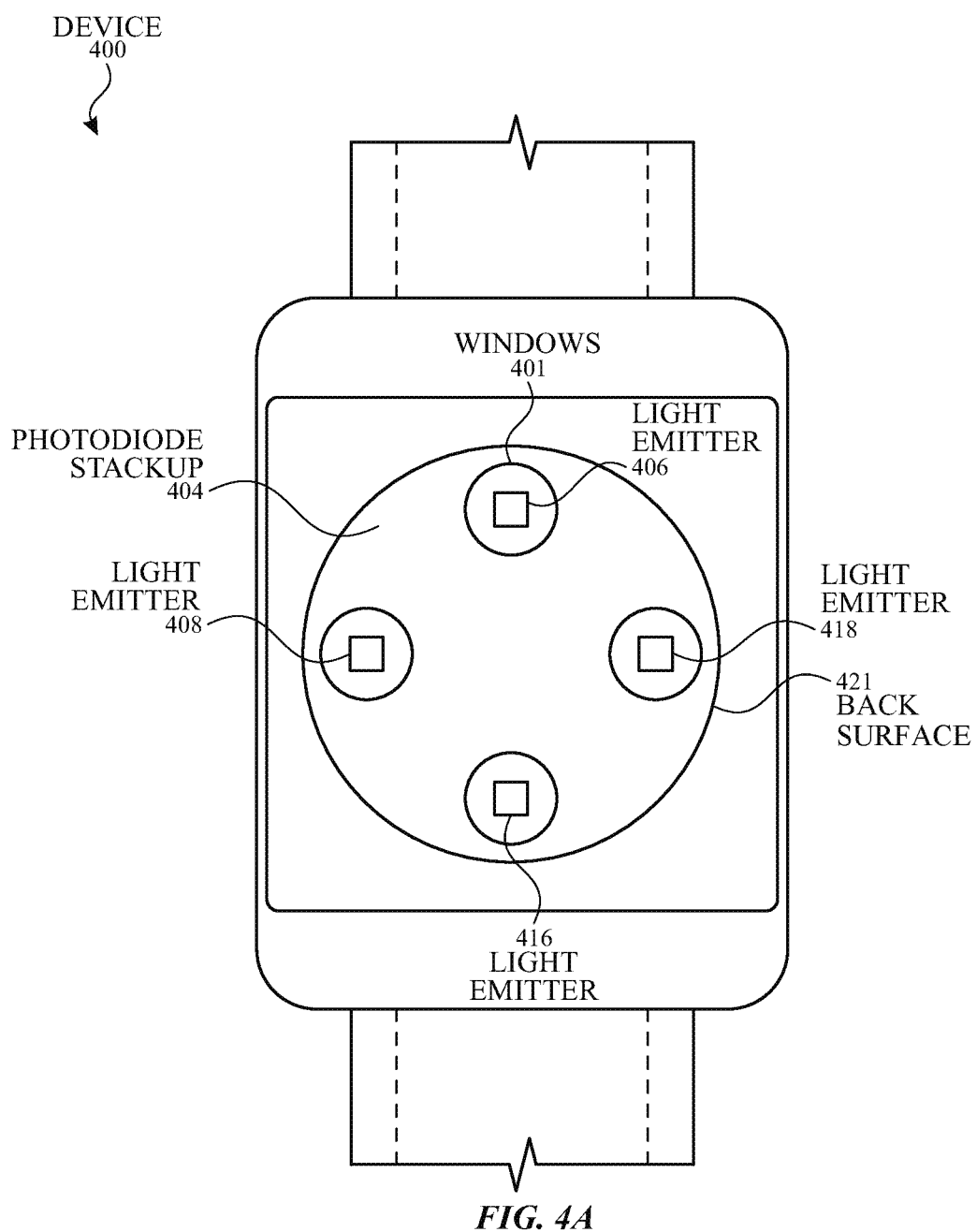
FIG. 4A illustrates a top view of an exemplary electronic device including integrated photodiodes disposed on a back surface according to examples of the disclosure.
Figure 4B:
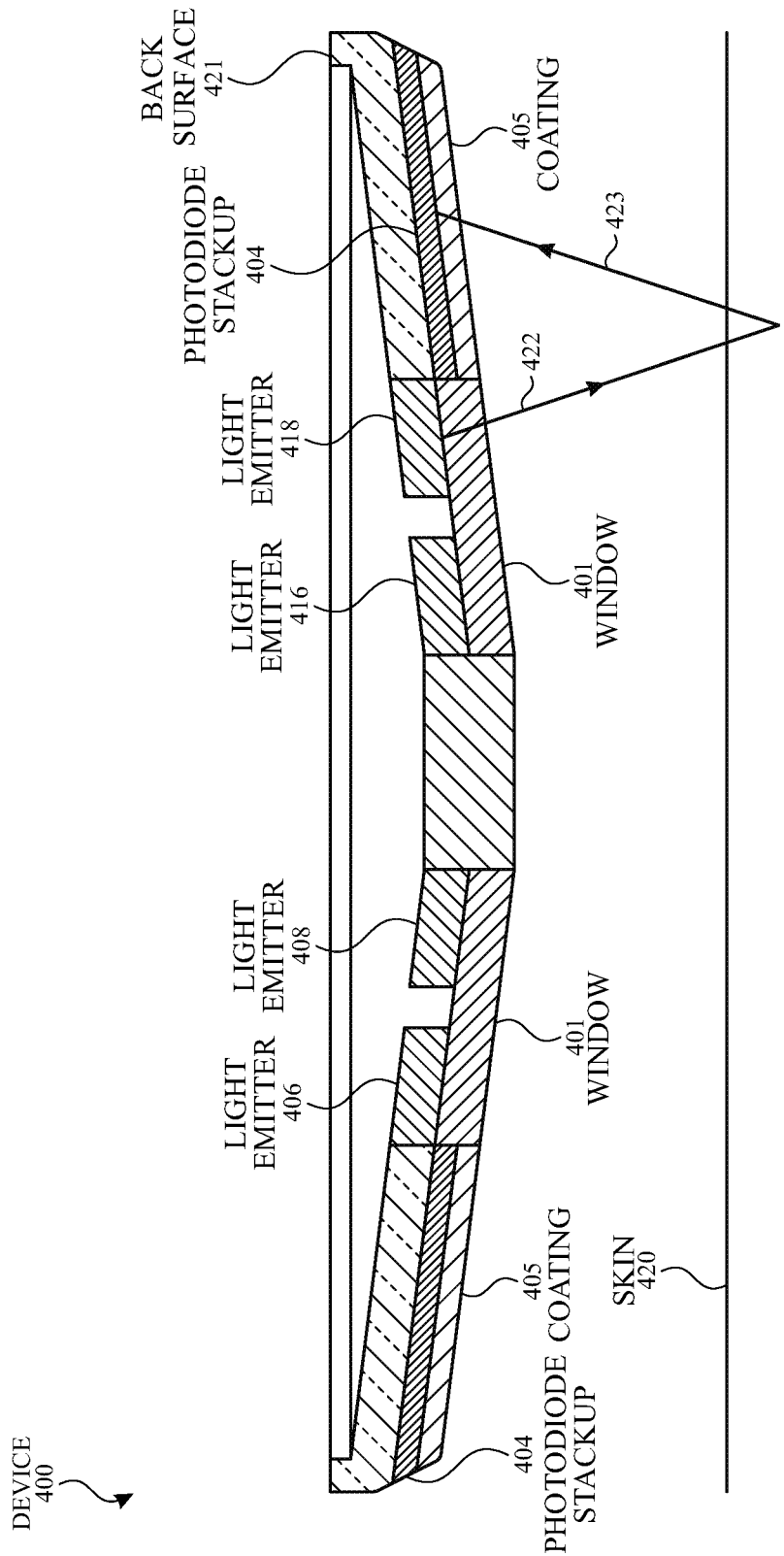
FIG. 4B illustrates a cross-sectional view of an exemplary electronic device including integrated photodiodes disposed on a back surface according to examples of the disclosure.

FIG. 4A illustrates a top view and FIG. 4B illustrates a cross-sectional view of an exemplary electronic device including integrated photodiodes disposed on a back surface according to examples of the disclosure. Device 400 can include light emitter 406, light emitter 408, light emitter 416, and light emitter 418 optically coupled to a window 401. In some examples, each light emitter can be optically coupled to a different window. In some examples, two or more light emitters can be optically coupled to the same window. Device 400 can be configured with one or more photodiodes located on an exterior surface. The exterior surface can be the surface of device 400 closer to skin 420 and/or the surface shared by windows 401. As illustrated in FIG. 4B, photodiode stackup 404 can be deposited on back surface 421, thereby minimizing any gap between the photodiode and skin 420. To protect photodiode stackup 404 from unwanted environmental conditions (e.g., dust, external forces, moisture, etc.), coating 405 can be deposited on photodiode stackup 404. In some examples, coating 405 can be located between photodiode stackup 404 and skin 420 (and/or the surface of window 401). The light emitters (e.g., light emitter 418) can be configured to emit light (e.g., light 422). Light can pass through window 401. A portion of light can be absorbed by one or more vasculature structures located in skin 420, and a portion of light (e.g., light 423) can reflect back. The reflection of light can pass through coating 405 and can be incident on the active area of photodiode stackup 404. Photodiode stackup 404 can generate one or more signals including reflected light information. The one or more signals can be transmitted to a controller or processor through one or more routing traces and/or pads (not shown). In some examples, routing traces and/or pads can be located along the perimeter of the back surface. In some examples, routing traces and/or pads can be located on the side of back surface opposite from the side with coating 405. By disposing photodiode stackup 404 on back surface 421, the photodiode can have a larger active area, which can enhance the photodiode's sensitivity and ability to detect signals having smaller intensities.

Figure 4C:
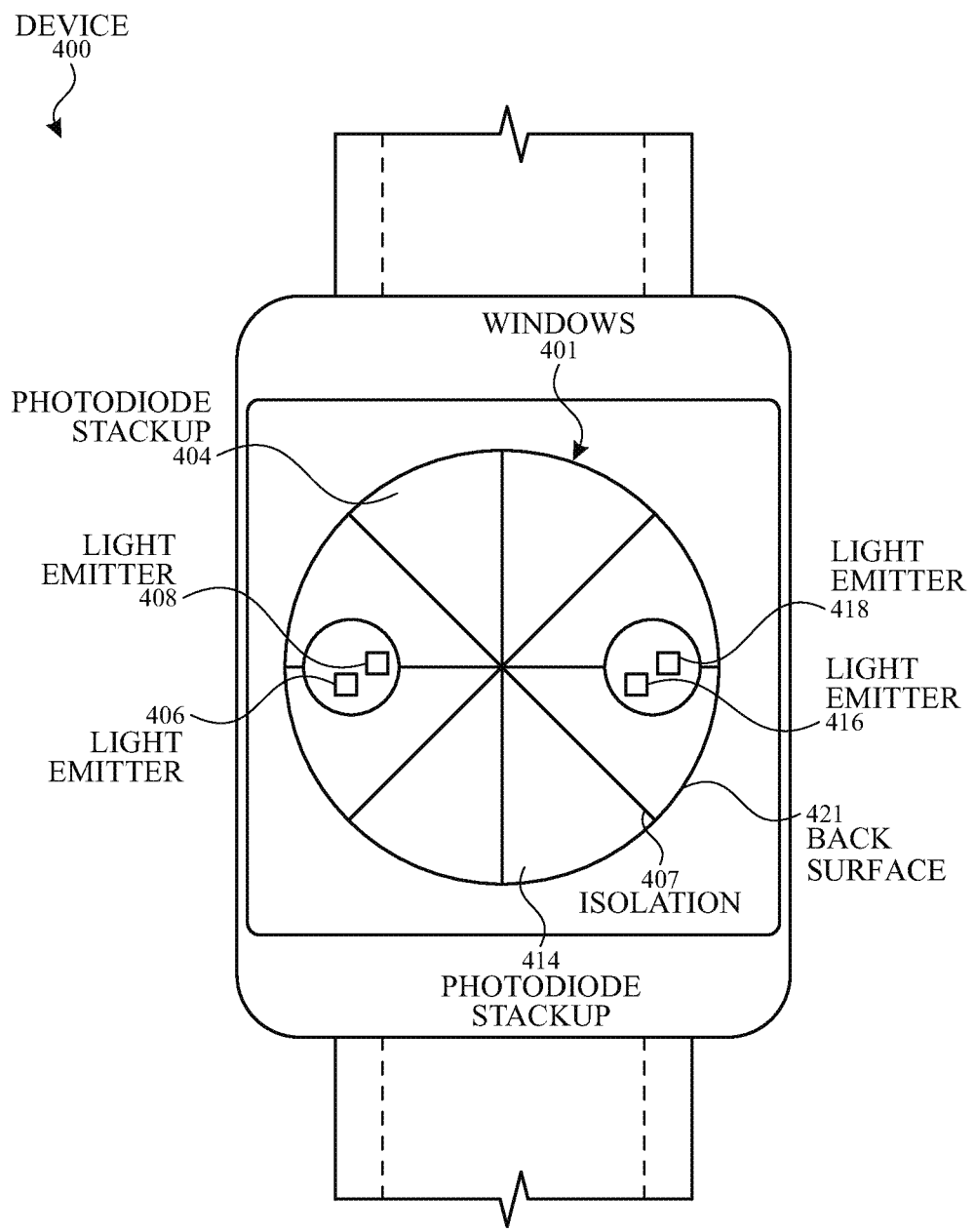
FIG. 4C illustrates a top view of an exemplary electronic device including a plurality of integrated photodiodes disposed on a back surface according to examples of the disclosure.

FIG. 4C illustrates a top view of an exemplary electronic device including a plurality of integrated photodiodes disposed on a back surface according to examples of the disclosure. In some examples, back surface 421 can be configured to support a plurality of photodiode stackups, such as photodiode stackup 404 and photodiode stackup 414. The plurality of photodiode stackups can be separated by isolation 407. Isolation 407 can include any type of material, including but not limited to, a dielectric insulator. In some examples, isolation 407 can include an air gap. In some examples, the plurality of photodiode stackups can appear to the human eye to be a single, continuous photodiode due to the controlled spacing of isolation 407 (e.g., less than 10 micron spacing). In some examples, isolation 407 can be 5 microns wide. In some examples, isolation 407 can be 1 micron wide. In some examples, isolation 407 can include routing traces.

Although FIG. 4C illustrates each of the plurality of photodiode stackups as having triangular shapes, examples of the disclosure can include any shape, including but not limited to, squares, circles, and ovals. Although FIG. 4C illustrates the plurality of photodiode stackups as deposited on back surface 421, examples of the disclosure can include the plurality of photodiode stacks deposited on any surface, including but not limited to, the housing (e.g., area outside of back surface 421) of device 400.

Figure 4D:
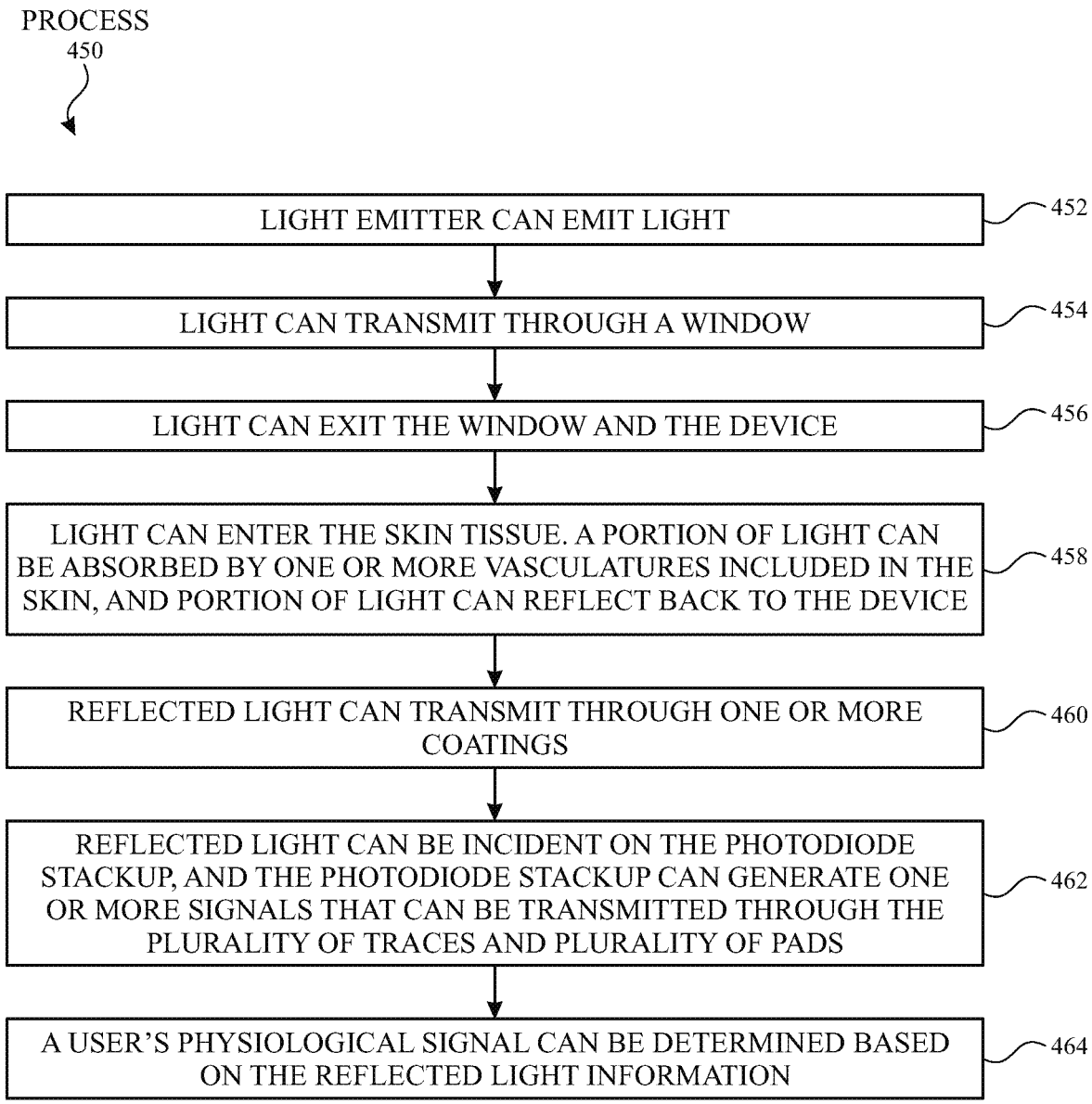
FIG. 4D illustrates an exemplary method for operating an electronic device including a plurality of integrated photodiodes according to examples of the disclosure.

FIG. 4D illustrates an exemplary method for operating an electronic device including a plurality of integrated photodiodes according to examples of the disclosure. In step 452 of process 450, light emitter (e.g., light emitter 408) can emit light towards the user (e.g., skin 420). In step 454 of process 450, light can pass through a window (e.g., window 401). In step 456 of process 450, light can exit the window (e.g., window 401) and the device (e.g., device 400). In step 458 of process 450, light can enter the skin tissue (e.g., skin 420). A portion of light can be absorbed by one or more vasculatures included in the skin, and a portion of light can reflect back to the device (e.g., device 400). In step 460 of process 450, the reflected light can pass through one or more coatings (e.g., coating 405). In step 462 of process 450, the reflected light can be incident on the photodiode stackup (e.g., photodiode stackup 404 and photodiode stackup 406). The photodiode stackup can generate one or more signals that can be transmitted to a processor or controller using the plurality of traces (e.g., plurality of traces 419) and the plurality of pads (e.g., plurality of pads 417). In step 464 of process 450, the user's physiological signal can be determined based on the reflected light information.

Figure 4E:
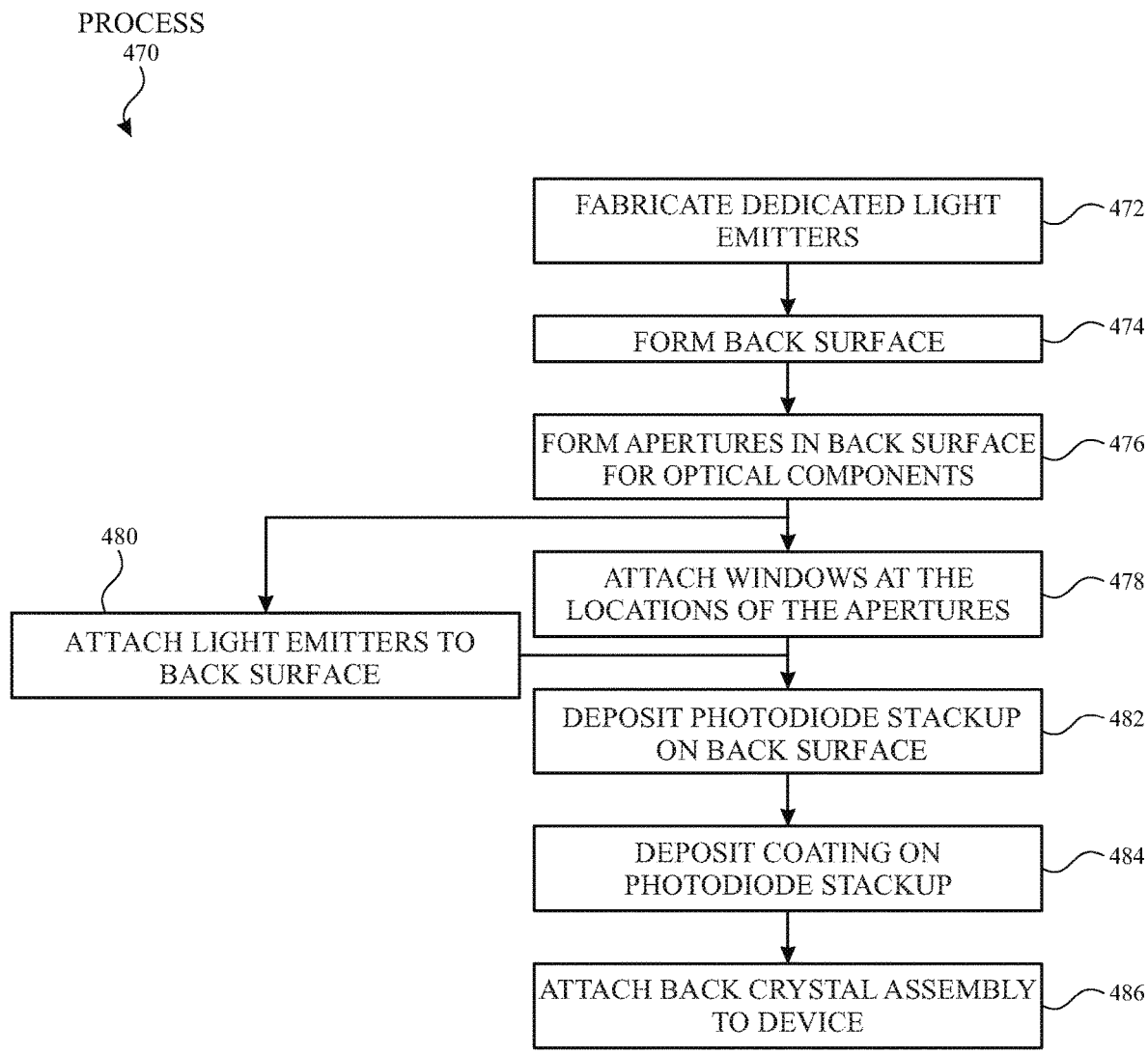
FIG. 4E illustrates an exemplary method for fabricating an exemplary electronic including one or more integrated photodiodes according to examples of the disclosure.

FIG. 4E illustrates an exemplary method for fabricating an exemplary electronic device including one or more integrated photodiodes according to examples of the disclosure. In step 472 of process 470, dedicated light emitters can be fabricated. In step 474 of process 470, the back surface (e.g., back surface 421) can be formed. In step 476 of process 470, apertures (e.g., apertures 402) can be formed for the optical components (e.g., light emitters and light sensors). In step 478 of process 470, windows (e.g., window 401) can be attached at the location of the apertures. In step 480 of process 470, the light emitters can be attached to the back surface (e.g., back surface 421). In step 482 of process 470, photodiode stackup (e.g., photodiode stackup 404 and photodiode stackup 406) can be deposited on the back surface (e.g., back surface 421). In step 484 of process 470, one or more coatings (e.g., coating 405) can be deposited on photodiode stackup (e.g., photodiode stackup 404 and photodiode stackup 406). In step 486 of process 470, the back surface assembly (i.e., back surface, attached light emitters and windows, and deposited light sensors) can be attached to the device (e.g., device 400).

Although the figures illustrate the photodiode stackup integrated into the back surface and utilized for PPG measurements, examples of the disclosure can include the photodiode stackup integrated into any material (e.g., housing) of the electronic device and utilized for any type of optical measurement (e.g., ambient light sensing). FIG. 5A illustrates a top view of an exemplary device including a sensor according to examples of the disclosure. Device 504 can include display 506 and border region 510. Display 506 can any type of touch sensitive component capable of sensing touch and/or hover. Border region 510 can be a region of device 504 located between edge of device 504 and display 506. Sensor 508 can be located in border region 510 and can be configured for sensing any type of light, including, but not limited to, ambient light. In some examples, sensor 508 can be placed in close proximity to the illuminating component (e.g., display or indicator lights) being controlled and can be facing the direction where light originates. For example, display 506 can include a display capable of projecting one or more images on the screen. Sensor 508 can be located in border region 510, which can be in close proximity to display 506 to sense the ambient light in the room or surrounding area. Based on the sensed ambient light, device 504 can adjust the brightness of the display 506.

In some examples, sensor 508 can be included in display 506. FIG. 5B illustrates a top view of an exemplary device including a sensor according to examples of the disclosure. Sensor 508 can be relocated to one or more locations closer to display 506 than a sensor located in border region 510 (as illustrated in FIG. 5A). In some examples, sensor 508 can be placed underneath display 506 in such a way as to allow the sensor to function through the display and/or any touch screen coupled to the display. In some examples, sensor 508 can be placed on top of display 506 in such a way as to not hinder the ability of the display to project content through or around the sensor. In some examples, sensor 508 can be incorporated into the structure of touch screen 506 (i.e., the sensor can be manufactured in the same process layers as the display and/or touch screen).

Figure 6:
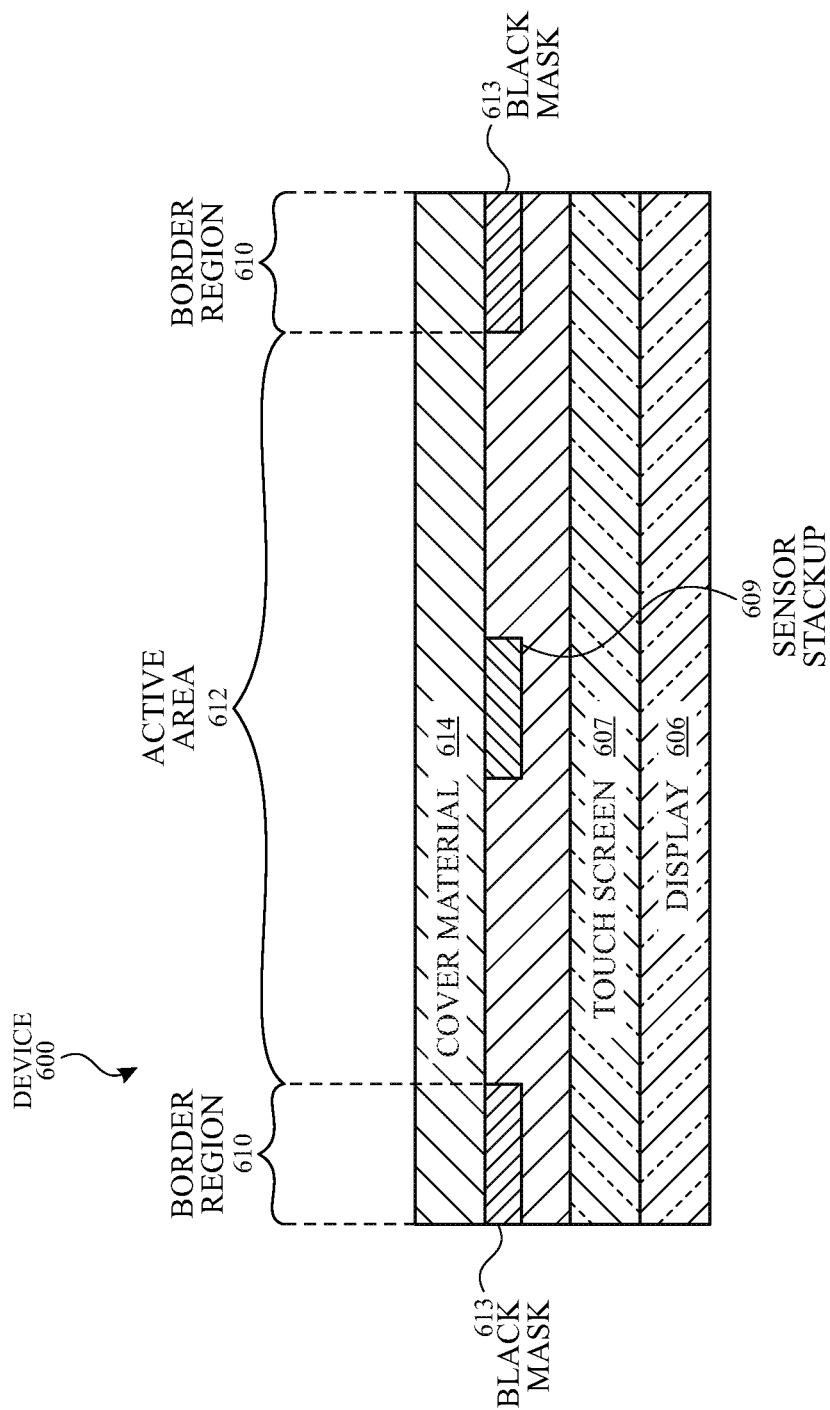
FIG. 6 illustrates a cross-sectional view of an exemplary electronic device including one or more integrated photodiodes according to examples of the disclosure.

To enhance the accuracy of sensed light and/or to reduce the number of layers in the stackup, examples of the disclosure can include one or more integrated photodiodes on a cover material and/or housing of the device. FIG. 6 illustrates a cross-sectional view of an exemplary electronic device including one or more integrated photodiodes according to examples of the disclosure. Device 600 can include cover material 614 and display 606. In some examples, device 600 can include a separate touch screen 607. In some examples, touch screen 607 can be integrated with display 606. Sensor stackup 609 can be located in active area 612 of device 600. Active area 612 can be any area of device 600 configured to allow light emitted from display 606 to pass through and/or allow a touch and/or hover object to be detected by touch screen 607. Instead of placing the sensor underneath (or on top of) display 606 and/or touch screen 607 or incorporating the sensor into the structure of display 606 and/or touch screen 607, sensor stackup 609 can be integrated into cover material 614 and/or housing 616. In some samples, sensor stackup 609 can disposed on cover material 614. In some examples, sensor stackup 609 can be contacting cover material 614. In some examples, sensor stackup 609 may not be separately packaged and/or fabricated. Sensor stackup 509 can include one or more layers that form the photodiode such as the P and N layers in a PN photodiode. In some examples, sensor stackup 609 can exclude a separate substrate (i.e., a base layer upon which a material is deposited onto). In some examples, one or more layers, excluding air, can be included in the sensor stackup 609 and can be located between cover material 614 and photodiode stackup 609. In some examples, the one or more layers, excluding air, can contact cover material 614. The one or more layers can include, but are not limited to, silicon dioxide and titanium dioxide. In this manner, sensor stackup 609 can be included in device 600 without the need for extra layers (e.g., a separate substrate), and measurement accuracy can be improved by having sensor stackup 609 located closer to the light source (e.g., ambient light).

Figure 7:
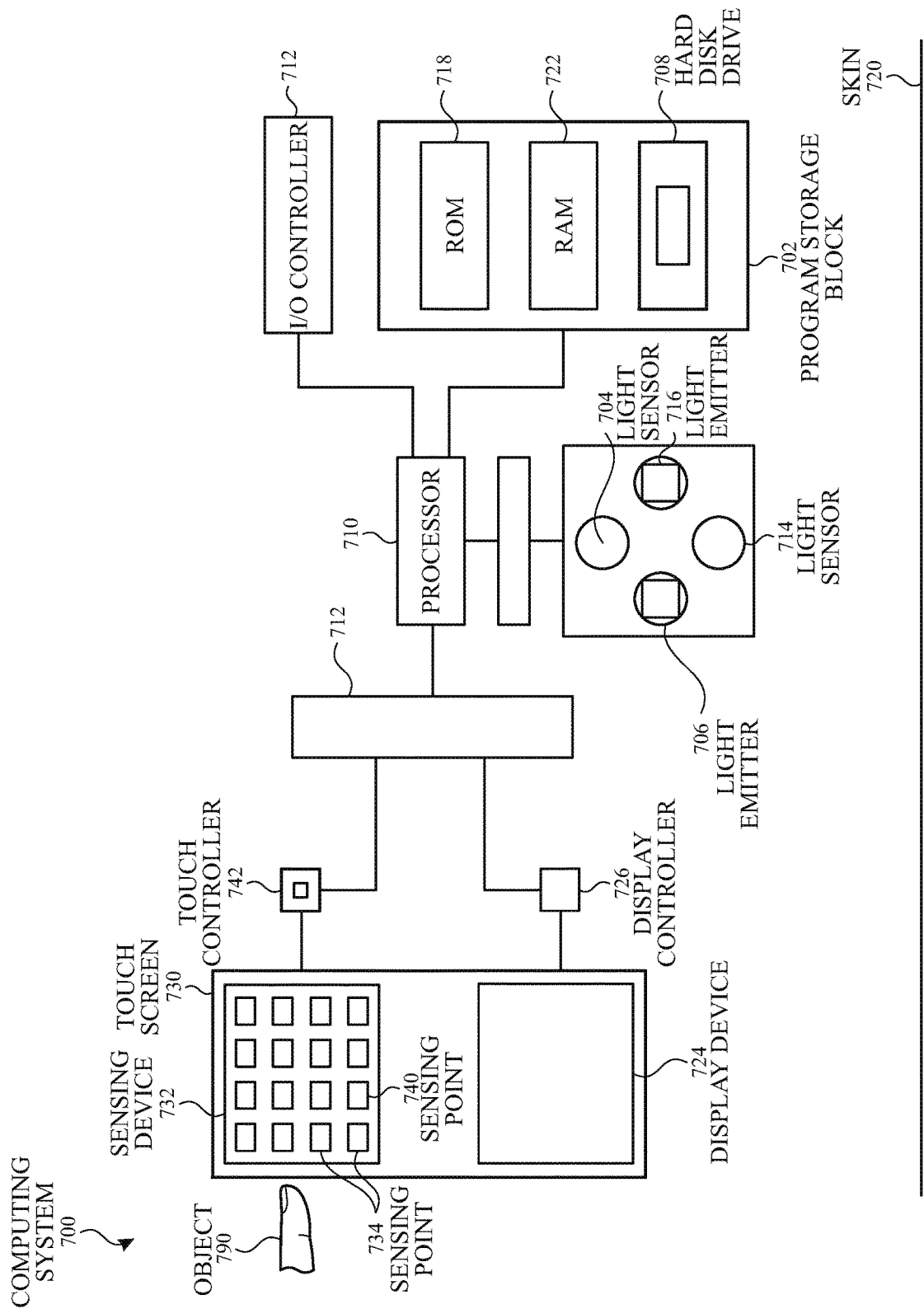
FIG. 7 illustrates an exemplary block diagram of a computing system comprising light emitters and light sensors for measuring a signal associated with a user's physiological state according to examples of the disclosure.

FIG. 7 illustrates an exemplary block diagram of a computing system comprising light emitters and light sensors for measuring a signal associated with a user's physiological state according to examples of the disclosure. Computing system 700 can correspond to any of the computing devices illustrated in FIGS. 1A-1C. Computing system 700 can include a processor 710 configured to execute instructions and to carry out operations associated with computing system 700. For example, using instructions retrieved from memory, processor 710 can control the reception and manipulation of input and output data between components of computing system 700. Processor 710 can be a single-chip processor or can be implemented with multiple components.

In some examples, processor 710 together with an operating system can operate to execute computer code and produce and use data. The computer code and data can reside within a program storage block 702 that can be operatively coupled to processor 710. Program storage block 702 can generally provide a place to hold data that is being used by computing system 700. Program storage block 702 can be any non-transitory computer-readable storage medium, and can store, for example, history and/or pattern data relating to PPG signal and perfusion index values measured by one or more light sensors such as light sensors 704. By way of example, program storage block 702 can include Read-Only Memory (ROM) 718, Random-Access Memory (RAM) 722, hard disk drive 708 and/or the like. The computer code and data could also reside on a removable storage medium and loaded or installed onto the computing system 700 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 700 can also include an input/output (I/O) controller 712 that can be operatively coupled to processor 710, or it can be a separate component as shown. I/O controller 712 can be configured to control interactions with one or more I/O devices. I/O controller 712 can operate by exchanging data between processor 710 and the I/O devices that desire to communicate with processor 710. The I/O devices and I/O controller 712 can communicate through a data link. The data link can be a one-way link or a two-way link. In some cases, I/O devices can be connected to I/O controller 712 through wireless connections. By way of example, a data link can correspond to PS/2, USB, Firewire, IR, RF, Bluetooth or the like.

Computing system 700 can include a display device 724 that can be operatively coupled to processor 710. Display device 724 can be a separate component (peripheral device) or can be integrated with processor 710 and program storage block 702 to form a desktop computer (e.g., all-in-one machine), a laptop, handheld or tablet computing device of the like. Display device 724 can be configured to display a graphical user interface (GUI) including perhaps a pointer or cursor as well as other information to the user. By way of example, display device 724 can be any type of display including a liquid crystal display (LCD), an electroluminescent display (ELD), a field emission display (FED), a light emitting diode display (LED), an organic light emitting diode display (OLED), or the like.

Display device 724 can be coupled to display controller 726 that can be coupled to processor 710. Processor 710 can send raw data to display controller 726, and display controller 726 can send signals to display device 724. Data can include voltage levels for a plurality of pixels in display device 724 to project an image. In some examples, processor 710 can be configured to process the raw data.

Computing system 700 can also include a touch screen 730 that can be operatively coupled to processor 710. Touch screen 730 can be a combination of sensing device 732 and display device 724, where the sensing device 732 can be a transparent panel that is positioned in front of display device 724 or integrated with display device 724. In some cases, touch screen 730 can recognize touches and the position and magnitude of touches on its surface. Touch screen 730 can report the touches to processor 710, and processor 710 can interpret the touches in accordance with its programming. For example, processor 710 can perform tap and event gesture parsing and can initiate a wake of the device or powering on one or more components in accordance with a particular touch.

Touch screen 730 can be coupled to a touch controller 740 that can acquire data from touch screen 730 and can supply the acquired data to processor 710. In some cases, touch controller 740 can be configured to send raw data to processor 710, and processor 710 can process the raw data. For example, processor 710 can receive data from touch controller 740 and can determine how to interpret the data. The data can include the coordinates of a touch as well as pressure exerted. In some examples, touch controller 740 can be configured to process raw data itself. That is, touch controller 740 can read signals from sensing points 734 located on sensing device 732 and can turn the signals into data that the processor 710 can understand.

Touch controller 742 can include one or more microcontrollers, each of which can monitor one or more sensing points 734. The microcontroller can, for example, correspond to an application specific integrated circuit (ASIC), which works with firmware to monitor the signals from sensing device 732, process the monitored signals, and report this information to processor 710.

One or both of display controller 726 and touch controller 740 can perform filtering and/or conversion processes. Filtering processes can be implemented to reduce a busy data stream to prevent processor 710 from being overloaded with redundant or non-essential data. The conversion processes can be implemented to adjust the raw data before sending or reporting them to processor 710.

In some examples, sensing device 732 can be based on capacitance. When two electrically conductive members come close to one another without actually touching, their electric fields can interact to form a capacitance. The first electrically conductive member can be one or more of the sensing points 734, and the second electrically conductive member can be an object 790 such as a finger. As object 790 approaches the surface of touch screen 730, a capacitance can form between object 790 and one or more sensing points 734 in close proximity to object 790. By detecting changes in capacitance at each of the sensing points 734 and noting the position of sensing points 734, touch controller 740 can recognize multiple objects, and determine the location, pressure, direction, speed and acceleration of object 790 as it moves across the touch screen 730. For example, touch controller 790 can determine whether the sensed touch is a finger, tap, or an object covering the surface.

Sensing device 732 can be based on self-capacitance or mutual capacitance. In self-capacitance, each of the sensing points 734 can be provided by an individually charged electrode. As object 790 approaches the surface of the touch screen 730, the object can capacitively couple to those electrodes in close proximity to object 790, thereby stealing charge away from the electrodes. The amount of charge in each of the electrodes can be measured by the touch controller 740 to determine the position of one or more objects when they touch or hover over the touch screen 730. In mutual capacitance, sensing device 732 can include a two layer grid of spatially separated lines or wires (not shown), although other configurations are possible. The upper layer can include lines in rows, while the lower layer can include lines in columns (e.g., orthogonal). Sensing points 734 can be provided at the intersections of the rows and columns. During operation, the rows can be charged, and the charge can capacitively couple from the rows to the columns. As object 790 approaches the surface of the touch screen 730, object 790 can capacitively couple to the rows in close proximity to object 790, thereby reducing the charge coupling between the rows and columns. The amount of charge in each of the columns can be measured by touch controller 740 to determine the position of multiple objects when they touch the touch screen 730.

Device 700 can also include one or more light emitters, such as light emitters 706, and one or more light sensors, such as integrated photodiodes 704, located proximate to skin 720 of a user. Light emitters 706 can be configured to generate light, and light sensors 704 can be configured to measure a light reflected or absorbed by skin 720, vasculature, and/or blood of the user. Light sensor 704 can send measured raw data to processor 710, and processor 710 can perform noise and/or artifact cancellation to determine the PPG signal and/or perfusion index. In some examples, processor 710 can store the raw data and/or processed information in a ROM 718 or RAM 722 for historical tracking or for future diagnostic purposes.

An electronic device is disclosed. The electronic device can comprise: one or more light sensors configured to detect a reflection of a light and configured to generate a signal indicative of the light, wherein the one or more light sensors includes a plurality of layers; one or more windows capable of allowing the light to pass through and configured to support the one or more light sensors; and a back surface coupled to the one or more windows, wherein at least one of the plurality of layers contacts one or more of the back surface and at least one of the one or more windows. Additionally or alternatively, in some examples, a gap between the one or more windows and a stackup included in the one or more light sensors is less than 0.8 mm. Additionally or alternatively, in some examples, a surface of the stackup contacts a surface of the one or more windows. Additionally or alternatively, in some examples, the stackup includes a p-type material, and the p-type material contacts a surface of the one or more windows. Additionally or alternatively, in some examples, the device further comprises: one or more layers located between the one or more windows and the one or more light sensors, wherein a surface of the one or more layers contacts the one or more windows and another surface of the one or more layers contacts the one or more light sensors, the one or more layers excluding air. Additionally or alternatively, in some examples, the electronic device excludes a separate substrate supporting the one or more light sensors. Additionally or alternatively, in some examples, the one or more light sensors are disposed on a surface of the one or more windows, the surface is opposite from an outer surface of the electronic device, and an active area of the one or more light sensors faces towards the outer surface of the electronic device. Additionally or alternatively, in some examples, the device further comprises: a plurality of conductive pads; and a plurality of routing traces, each routing trace coupled to one of the one or more light emitters or the one or more light sensors and configured to route one or more signals between at least one of the one or more light emitters or the one or more light sensors and at least one of the plurality of conductive pads, wherein the plurality of routing traces and the plurality of conductive pads are disposed a surface of the back surface, the surface of the back surface located away from an outer surface of the electronic device. Additionally or alternatively, in some examples, the device further comprises: a plurality of conductive pads; a plurality of vias; a plurality of first routing traces, each first routing trace coupled to one of the one or more light emitters or the one or more light sensors and configured to route one or more signals between at least one of the one or more light emitters or the one or more light sensors and at least one of the plurality of vias; and a plurality of second routing traces, each second routing trace coupled to at least one of the plurality of vias and configured to route one or more signals between the at least one of the plurality of vias and at a least one of the plurality of conductive pads. Additionally or alternatively, in some examples, the device further comprises: one or more conductive pads configured to route one or more signals to at least one of the one or more light emitters or at least one of the one or more light sensors, wherein the one or more conductive pads are located in an outer perimeter of the back surface. Additionally or alternatively, in some examples, the one or more light sensors are disposed on an outer surface of the electronic device. Additionally or alternatively, in some examples, the device further comprises: a coating contacting the one or more light sensors and configured to protect the one or more light sensors, wherein the one or more light sensors are located between the coating and the back surface. Additionally or alternatively, in some examples, the coating includes a black ink. Additionally or alternatively, in some examples, at least one of the one or more light sensors is a black photodiode. Additionally or alternatively, in some examples, a surface of a stackup included in the one or more light sensors contacts the back surface. Additionally or alternatively, in some examples, the surface is opposite from an inner surface of the electronic device and an active area of the one or more light sensors faces towards an outer surface of the electronic device. Additionally or alternatively, in some examples, the one or more light sensors includes at least two light sensors, wherein a total active area of the at least two light sensors substantially occupies a full area of the back surface. Additionally or alternatively, in some examples, the device further comprises: an isolation located between the at least two light sensors and configured to electrically isolate the at least two light sensors. Additionally or alternatively, in some examples, the at least two light sensors are spatially separated by at least 5 microns.

A method for detecting physiological signals is disclosed. The method comprises: emitting light from one or more light emitters to one or more windows without first transmitting through a layer of air; allowing light to pass through the one or more windows; detecting the light from tissue; and generating one or more signals indicative of the reflection of light. Additionally or alternatively, in some examples, emitting light from the one or more light emitters to the one or more windows comprises: emitting light from the one or more light emitters to a coating, and allow light to pass through the coating to the one or more windows. Additionally or alternatively, in some examples, emitting light from the one or more light emitters to the one or more windows comprises: transmitting light through a sensor-window interface. Additionally or alternatively, in some examples, emitting light from the one or more light emitters to the one or more windows comprises: transmitting light through a layer-window interface, wherein the layer excludes air.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A mobile electronic device comprising:
one or more light sensors configured to detect a light and configured to generate a signal indicative of the light;
one or more windows capable of allowing the light to pass through and configured to support the one or more light sensors; and
a back surface of a housing of the mobile electronic device coupled to the one or more windows, wherein:
the one or more light sensors includes a plurality of layers comprising at least one light sensing film;
an active area of the one or more light sensors covers a full area of the one or more windows;
the one or more light sensors includes at least two light sensors;
a total active area of the at least two light sensors substantially occupies a full area of the back surface of the housing of the mobile electronic device;
the one or more light sensors do not have a light sensor substrate on the side of the one or more light sensors opposite the one or more windows;
the at least one light sensing film is adjacent to at least one window of the one or more windows, or a second film that is adjacent to the at least one window; and
at least one of the plurality of layers contacts one or more of:
the back surface of the housing of the mobile electronic device, the at least one window, or the second film.

2. The mobile electronic device of claim 1, wherein:
the one or more light sensors comprises a stackup; and
a surface of the stackup contacts a surface of the one or more windows.

3. The mobile electronic device of claim 2, wherein the stackup includes a p-type material, and the p-type material contacts the surface of the one or more windows.

4. The mobile electronic device of claim 1, further comprising:
the second film located between the one or more windows and the one or more light sensors, wherein a surface of the second film contacts the one or more windows and another surface of the second film contacts the one or more light sensors, the second film excluding air.

5. The mobile electronic device of claim 1, wherein the one or more light sensors are disposed on a surface of the one or more windows, the surface is opposite from the back surface of the housing of the mobile electronic device, and an active area of the one or more light sensors faces towards the back surface of the housing of the mobile electronic device.

6. The mobile electronic device of claim 1, further comprising:
a plurality of conductive pads; and
a plurality of routing traces, each routing trace coupled to one of one or more light emitters or the one or more light sensors and configured to route one or more signals between at least one of the one or more light emitters or the one or more light sensors and at least one of the plurality of conductive pads,
wherein the plurality of routing traces and the plurality of conductive pads are disposed on a surface of a back surface, the surface of the back surface located away from the back surface of the housing of the mobile electronic device.

7. The mobile electronic device of claim 1, further comprising:
a plurality of conductive pads;
a plurality of vias;
a plurality of first routing traces, each first routing trace coupled to a one of the one or more light emitters or the one or more light sensors and configured to route one or more signals between at least one of the one or more light emitters or the one or more light sensors and at least one of the plurality of vias; and
a plurality of second routing traces, each second routing trace coupled to at least one of the plurality of vias and configured to route one or more signals between the at least one of the plurality of vias and at a least one of the plurality of conductive pads.

8. The mobile electronic device of claim 1, further comprising:
one or more conductive pads configured to route one or more signals to at least one of a one or more light emitters or at least one of the one or more light sensors,
wherein the one or more conductive pads are located in an outer perimeter of the back surface of the housing of the mobile electronic device.

9. The mobile electronic device of claim 1, further comprising:
a coating contacting the one or more light sensors and configured to protect the one or more light sensors, wherein the one or more light sensors are located between the coating and the back surface of the housing of the mobile electronic device.

10. The mobile electronic device of claim 9, wherein the coating includes a black ink.

11. The mobile electronic device of claim 1, wherein at least one of the one or more light sensors is a black photodiode.

12. The mobile electronic device of claim 1, wherein a surface of one of the plurality of layers included in the one or more light sensors is opposite from an inner surface of the electronic device and an active area of the one or more light sensors faces towards the back surface of the housing of the mobile electronic device.

13. The mobile electronic device of claim 1, further comprising:
an isolation located between the at least two light sensors and configured to electrically isolate the at least two light sensors.

14. A method for detecting physiological signals, comprising:
emitting light from one or more light emitters to one or more windows without first transmitting through a layer of air;
allowing the emitted light to pass through the one or more windows coupled to a back surface of a housing of a mobile electronic device;
detecting a portion of a reflected light from tissue using one or more light sensors, the one or more light sensors comprising a light sensing film adjacent to at least one of:
the back surface of the housing of the mobile electronic device;
a window of the one or more windows; or
a second film that is adjacent to the window; and
generating, using the one or more light sensors, one or more signals indicative of the reflected light, wherein:
an active area of the one or more light sensors covers a full area of the one or more windows;
the one or more light sensors includes at least two light sensors;
a total active area of the at least two light sensors substantially occupies a full area of the back surface of the housing of the mobile electronic device; and
the one or more light sensors do not have a light sensor substrate on the side of the one or more light sensors opposite the window.

15. The method of claim 14, wherein emitting light from the one or more light emitters to the one or more windows comprises:
emitting light from the one or more light emitters to a coating, and
allowing the emitted light to pass through the coating to the one or more windows.

16. The method of claim 15, wherein emitting light from the one or more light emitters to the one or more windows comprises:
transmitting the reflected light through a sensor-window interface.

17. The method of claim 15, wherein emitting light from the one or more light emitters to the one or more windows comprises:
transmitting the reflected light through a second film-window interface, wherein the second film excludes air.

* * * * *